United States Patent
Gore et al.

(10) Patent No.: US 11,680,284 B2
(45) Date of Patent: *Jun. 20, 2023

(54) SCREENING FOR STRUCTURAL VARIANTS

(71) Applicant: Molecular Loop Biosciences, Inc., Allston, MA (US)

(72) Inventors: Athurva Gore, Cambridge, MA (US); Mark Umbarger, Brookline, MA (US)

(73) Assignee: Moledular Loop Biosciences, Inc., Newton, MA (US)

( * ) Notice: Subject to any disclaimer, the term of this patent is extended or adjusted under 35 U.S.C. 154(b) by 149 days.

This patent is subject to a terminal disclaimer.

(21) Appl. No.: 16/117,248

(22) Filed: Aug. 30, 2018

(65) Prior Publication Data
US 2018/0371533 A1    Dec. 27, 2018

Related U.S. Application Data

(63) Continuation of application No. 14/989,073, filed on Jan. 6, 2016, now Pat. No. 10,066,259.
(Continued)

(51) Int. Cl.
*C12Q 1/6827* (2018.01)
*C12Q 1/6869* (2018.01)
(Continued)

(52) U.S. Cl.
CPC .......... *C12Q 1/6827* (2013.01); *C12Q 1/686* (2013.01); *C12Q 1/6809* (2013.01); *C12Q 1/6869* (2013.01)

(58) Field of Classification Search
CPC .................................. C07H 21/00; C12Q 1/68
See application file for complete search history.

(56) References Cited

U.S. PATENT DOCUMENTS 4,683,195 A    7/1987  Mullis et al.
4,683,202 A    7/1987  Mullis
(Continued)

FOREIGN PATENT DOCUMENTS

EP    1 321 477 A1    6/2003
EP    1 564 306 A2    8/2005
(Continued)

OTHER PUBLICATIONS

Ceska et al., Structure-specific DNA cleavage by 5 nucleases. Trends in Biochemical Sciences (Sep. 1998) (Year: 1998).*
(Continued)

*Primary Examiner* — Ethan C Whisenant
(74) *Attorney, Agent, or Firm* — Withers Bergman, LLP; Thomas C. Meyers

(57) ABSTRACT

The invention relates to carrier screening and methods for describing a structural variant, such as a large rearrangement or chromosomal abnormality, in a person's genome using probes that are designed to determine the person's genetic sequence and reveal substitution mutations and small structural variants. Identifying a structural variant may include exposing a nucleic acid to a plurality of probes. Each probe has a linked pair of targeting arms designed to hybridize upstream and downstream of a target in a genome. The method includes hybridizing two of the probes to the nucleic acid and attaching the two probes together to create an inter-probe product as well as detecting the inter-probe product and reporting a structural variant of the genome in the nucleic acid.

20 Claims, 5 Drawing Sheets

Related U.S. Application Data

(60) Provisional application No. 62/100,254, filed on Jan. 6, 2015.

(51) Int. Cl.
    *C12Q 1/6809*     (2018.01)
    *C12Q 1/686*     (2018.01)

(56) References Cited

U.S. PATENT DOCUMENTS

| | | |
|---|---|---|
| 4,988,617 A | 1/1991 | Landegren et al. |
| 5,060,980 A | 10/1991 | Johnson et al. |
| 5,210,015 A | 5/1993 | Gelfand et al. |
| 5,234,809 A | 8/1993 | Boom et al. |
| 5,242,794 A | 9/1993 | Whiteley et al. |
| 5,348,853 A | 9/1994 | Wang et al. |
| 5,434,049 A | 7/1995 | Okano et al. |
| 5,459,307 A | 10/1995 | Klotz, Jr. |
| 5,486,686 A | 1/1996 | Zdybel, Jr. et al. |
| 5,491,224 A | 2/1996 | Bittner et al. |
| 5,494,810 A | 2/1996 | Barany et al. |
| 5,567,583 A | 10/1996 | Wang et al. |
| 5,583,024 A | 12/1996 | McElroy et al. |
| 5,604,097 A | 2/1997 | Brenner |
| 5,636,400 A | 6/1997 | Young |
| 5,674,713 A | 10/1997 | McElroy et al. |
| 5,695,934 A | 12/1997 | Brenner |
| 5,700,673 A | 12/1997 | McElroy et al. |
| 5,701,256 A | 12/1997 | Marr et al. |
| 5,830,064 A | 11/1998 | Bradish et al. |
| 5,846,719 A | 12/1998 | Brenner et al. |
| 5,863,722 A | 1/1999 | Brenner |
| 5,866,337 A | 2/1999 | Schon |
| 5,869,252 A | 2/1999 | Bouma et al. |
| 5,869,717 A | 2/1999 | Frame et al. |
| 5,871,921 A | 2/1999 | Landegren et al. |
| 5,888,788 A | 3/1999 | De Miniac |
| 5,942,391 A | 8/1999 | Zhang et al. |
| 5,971,921 A | 10/1999 | Timbel |
| 5,993,611 A | 11/1999 | Moroney, III et al. |
| 5,994,056 A | 11/1999 | Higuchi |
| 6,020,127 A | 2/2000 | MacKenzie et al. |
| 6,033,854 A | 3/2000 | Kumit et al. |
| 6,033,872 A | 3/2000 | Bergsma et al. |
| 6,100,099 A | 8/2000 | Gordon et al. |
| 6,138,077 A | 10/2000 | Brenner |
| 6,150,516 A | 11/2000 | Brenner et al. |
| 6,171,785 B1 | 1/2001 | Higuchi |
| 6,172,214 B1 | 1/2001 | Brenner |
| 6,172,218 B1 | 1/2001 | Brenner |
| 6,197,508 B1 | 3/2001 | Stanley |
| 6,197,574 B1 | 3/2001 | Miyamoto et al. |
| 6,210,891 B1 | 4/2001 | Nyren et al. |
| 6,221,603 B1 * | 4/2001 | Mahtani ............... C12Q 1/6816 435/6.12 |
| 6,223,128 B1 | 4/2001 | Allex et al. |
| 6,235,472 B1 | 5/2001 | Landegren et al. |
| 6,235,475 B1 | 5/2001 | Brenner et al. |
| 6,235,501 B1 | 5/2001 | Gautsch et al. |
| 6,235,502 B1 | 5/2001 | Weissman et al. |
| 6,258,568 B1 | 7/2001 | Nyren |
| 6,274,320 B1 | 8/2001 | Rothberg et al. |
| 6,306,597 B1 | 10/2001 | Macevicz |
| 6,352,828 B1 | 3/2002 | Brenner |
| 6,360,235 B1 | 3/2002 | Tilt et al. |
| 6,361,940 B1 | 3/2002 | Van Ness et al. |
| 6,403,320 B1 | 6/2002 | Read et al. |
| 6,462,254 B1 | 10/2002 | Vernachio et al. |
| 6,489,105 B1 | 12/2002 | Matlashewski et al. |
| 6,558,928 B1 | 5/2003 | Landegren |
| 6,569,920 B1 | 5/2003 | Wen et al. |
| 6,582,938 B1 | 6/2003 | Su et al. |
| 6,585,938 B1 | 7/2003 | Machida et al. |
| 6,613,516 B1 | 9/2003 | Christians et al. |
| 6,714,874 B1 | 3/2004 | Myers et al. |
| 6,716,580 B2 | 4/2004 | Gold et al. |
| 6,719,449 B1 | 4/2004 | Laugharn, Jr. et al. |
| 6,818,395 B1 | 11/2004 | Quake et al. |
| 6,828,100 B1 | 12/2004 | Ronaghi |
| 6,833,246 B2 | 12/2004 | Balasubramanian |
| 6,858,412 B2 | 2/2005 | Willis et al. |
| 6,911,345 B2 | 6/2005 | Quake et al. |
| 6,913,879 B1 | 7/2005 | Schena |
| 6,927,024 B2 | 8/2005 | Dodge et al. |
| 6,941,317 B1 | 9/2005 | Chamberlin et al. |
| 6,948,843 B2 | 9/2005 | Laugham, Jr. et al. |
| 7,034,143 B1 | 4/2006 | Preparata et al. |
| 7,041,481 B2 | 5/2006 | Anderson et al. |
| 7,049,077 B2 | 5/2006 | Yang |
| 7,057,026 B2 | 6/2006 | Barnes et al. |
| 7,071,324 B2 | 7/2006 | Preparata et al. |
| 7,074,564 B2 | 7/2006 | Landegren |
| 7,074,586 B1 | 7/2006 | Cheronis et al. |
| 7,115,400 B1 | 10/2006 | Adessi et al. |
| 7,169,560 B2 | 1/2007 | Lapidus et al. |
| 7,211,390 B2 | 5/2007 | Rothberg et al. |
| 7,232,656 B2 | 6/2007 | Balasubramanian et al. |
| 7,244,559 B2 | 7/2007 | Rothberg et al. |
| RE39,793 E | 8/2007 | Brenner |
| 7,264,929 B2 | 9/2007 | Rothberg et al. |
| 7,282,337 B1 | 10/2007 | Harris |
| 7,297,518 B2 | 11/2007 | Quake et al. |
| 7,320,860 B2 | 1/2008 | Landegren et al. |
| 7,323,305 B2 | 1/2008 | Leamon et al. |
| 7,335,762 B2 | 2/2008 | Rothberg et al. |
| 7,351,528 B2 | 4/2008 | Landegren |
| 7,393,665 B2 | 7/2008 | Brenner |
| 7,510,829 B2 | 3/2009 | Faham et al. |
| 7,523,117 B2 | 4/2009 | Zhang et al. |
| 7,537,889 B2 | 5/2009 | Sinha et al. |
| 7,537,897 B2 | 5/2009 | Brenner et al. |
| 7,544,473 B2 | 6/2009 | Brenner |
| 7,582,431 B2 | 9/2009 | Drmanac et al. |
| 7,598,035 B2 | 10/2009 | Macevicz |
| 7,629,151 B2 | 12/2009 | Gold et al. |
| 7,642,056 B2 | 1/2010 | Ahn et al. |
| 7,666,593 B2 | 2/2010 | Lapidus |
| 7,700,323 B2 | 4/2010 | Willis et al. |
| 7,774,962 B1 | 8/2010 | Ladd |
| 7,776,616 B2 | 8/2010 | Heath et al. |
| RE41,780 E | 9/2010 | Anderson et al. |
| 7,790,388 B2 | 9/2010 | Landegren et al. |
| 7,809,509 B2 | 10/2010 | Milosavljevic |
| 7,835,871 B2 | 11/2010 | Kain et al. |
| 7,862,999 B2 | 1/2011 | Zheng et al. |
| 7,865,534 B2 | 1/2011 | Genstruct |
| 7,883,849 B1 | 2/2011 | Dahl |
| 7,957,913 B2 | 6/2011 | Chinitz et al. |
| 7,960,120 B2 | 6/2011 | Rigatti et al. |
| 7,985,716 B2 | 7/2011 | Yershov et al. |
| 7,993,880 B2 | 8/2011 | Willis et al. |
| 8,024,128 B2 | 9/2011 | Rabinowitz et al. |
| 8,114,027 B2 | 2/2012 | Triva |
| 8,165,821 B2 | 4/2012 | Zhang |
| 8,209,130 B1 | 6/2012 | Kennedy et al. |
| 8,283,116 B1 | 10/2012 | Bhattacharyya et al. |
| 8,462,161 B1 | 6/2013 | Barber |
| 8,463,895 B2 | 6/2013 | Arora et al. |
| 8,474,228 B2 | 7/2013 | Adair et al. |
| 8,496,166 B2 | 7/2013 | Burns et al. |
| 8,529,744 B2 | 9/2013 | Marziali et al. |
| 8,738,300 B2 | 5/2014 | Porreca et al. |
| 8,778,609 B1 | 7/2014 | Umbarger |
| 8,812,422 B2 | 8/2014 | Nizzari et al. |
| 8,847,799 B1 | 9/2014 | Kennedy et al. |
| 8,976,049 B2 | 3/2015 | Kennedy et al. |
| 9,074,244 B2 | 7/2015 | Sparks et al. |
| 9,115,387 B2 | 8/2015 | Umbarger |
| 9,228,233 B2 | 1/2016 | Kennedy et al. |
| 9,292,527 B2 | 3/2016 | Kennedy et al. |
| 9,535,920 B2 | 1/2017 | Kennedy et al. |
| 9,567,639 B2 | 2/2017 | Oliphant et al. |
| 9,677,124 B2 | 6/2017 | Umbarger |
| 10,066,259 B2 * | 9/2018 | Gore ............... C12Q 1/6869 |

(56) References Cited

U.S. PATENT DOCUMENTS

| | | |
|---|---|---|
| 10,202,637 B2 | 2/2019 | Umbarger |
| 10,227,635 B2 | 3/2019 | Umbarger et al. |
| 10,604,799 B2 | 3/2020 | Porreca et al. |
| 10,683,533 B2 | 6/2020 | Umbarger et al. |
| 2001/0007742 A1 | 7/2001 | Landergren |
| 2001/0046673 A1 | 11/2001 | French et al. |
| 2002/0001800 A1 | 1/2002 | Lapidus |
| 2002/0040216 A1 | 4/2002 | Dumont et al. |
| 2002/0042052 A1 | 4/2002 | Nilsen et al. |
| 2002/0058250 A1* | 5/2002 | Firth .............. C12Q 1/6855 435/6.12 |
| 2002/0091666 A1 | 7/2002 | Rice et al. |
| 2002/0164629 A1 | 11/2002 | Quake et al. |
| 2002/0172954 A1 | 11/2002 | Mao et al. |
| 2002/0182609 A1 | 12/2002 | Arcot |
| 2002/0187496 A1 | 12/2002 | Andersson et al. |
| 2002/0190663 A1 | 12/2002 | Rasmussen |
| 2003/0166057 A1 | 9/2003 | Hildebrand et al. |
| 2003/0175709 A1 | 9/2003 | Murphy et al. |
| 2003/0177105 A1 | 9/2003 | Xiao et al. |
| 2003/0203370 A1 | 10/2003 | Yakhini et al. |
| 2003/0208454 A1 | 11/2003 | Rienhoff et al. |
| 2003/0224380 A1* | 12/2003 | Becker ............ C12Q 1/6883 435/6.11 |
| 2003/0224384 A1 | 12/2003 | Sayood et al. |
| 2004/0029264 A1 | 2/2004 | Robbins |
| 2004/0053275 A1 | 3/2004 | Shafer |
| 2004/0106112 A1 | 6/2004 | Nilsson et al. |
| 2004/0121373 A1 | 6/2004 | Friedlander et al. |
| 2004/0142325 A1 | 7/2004 | Mintz et al. |
| 2004/0152108 A1 | 8/2004 | Keith et al. |
| 2004/0161773 A1 | 8/2004 | Rogan et al. |
| 2004/0170965 A1 | 9/2004 | Scholl et al. |
| 2004/0171051 A1 | 9/2004 | Holloway |
| 2004/0175719 A1 | 9/2004 | Christians |
| 2004/0197813 A1 | 10/2004 | Hoffman et al. |
| 2004/0209299 A1 | 10/2004 | Pinter et al. |
| 2005/0003369 A1 | 1/2005 | Christians et al. |
| 2005/0026204 A1 | 2/2005 | Landegren |
| 2005/0032095 A1 | 2/2005 | Wigler et al. |
| 2005/0048505 A1 | 3/2005 | Fredrick et al. |
| 2005/0059048 A1 | 3/2005 | Gunderson et al. |
| 2005/0100900 A1 | 5/2005 | Kawashima et al. |
| 2005/0112590 A1 | 5/2005 | Boom et al. |
| 2005/0186589 A1 | 8/2005 | Kowalik et al. |
| 2005/0214811 A1 | 9/2005 | Margulies et al. |
| 2005/0239733 A1* | 10/2005 | Jurk ................ C12N 15/117 514/44 A |
| 2005/0244879 A1 | 11/2005 | Schumm et al. |
| 2005/0250147 A1 | 11/2005 | Macevicz |
| 2005/0272065 A1 | 12/2005 | Lakey et al. |
| 2006/0008824 A1 | 1/2006 | Ronaghi et al. |
| 2006/0019304 A1 | 1/2006 | Hardenbol et al. |
| 2006/0024681 A1 | 2/2006 | Smith et al. |
| 2006/0030536 A1* | 2/2006 | Yu .................. A61K 45/06 514/44 A |
| 2006/0078894 A1 | 4/2006 | Winkler et al. |
| 2006/0149047 A1 | 7/2006 | Nanduri et al. |
| 2006/0177837 A1 | 8/2006 | Borozan et al. |
| 2006/0183132 A1 | 8/2006 | Fu et al. |
| 2006/0192047 A1 | 8/2006 | Goossen |
| 2006/0195269 A1 | 8/2006 | Yeatman et al. |
| 2006/0246500 A1 | 11/2006 | Browne |
| 2006/0263789 A1 | 11/2006 | Kincaid |
| 2006/0281098 A1* | 12/2006 | Miao ............... C12Q 2521/501 435/6.14 |
| 2006/0286577 A1 | 12/2006 | Jia |
| 2006/0292585 A1 | 12/2006 | Nautiyal et al. |
| 2006/0292611 A1 | 12/2006 | Berka et al. |
| 2007/0009925 A1 | 1/2007 | Fang et al. |
| 2007/0020640 A1 | 1/2007 | McCloskey et al. |
| 2007/0042369 A1 | 2/2007 | Reese et al. |
| 2007/0092883 A1 | 4/2007 | Schouten et al. |
| 2007/0114362 A1 | 5/2007 | Feng et al. |
| 2007/0128624 A1 | 6/2007 | Gormley et al. |
| 2007/0161013 A1 | 7/2007 | Hantash |
| 2007/0162983 A1 | 7/2007 | Hesterkamp et al. |
| 2007/0166705 A1 | 7/2007 | Milton et al. |
| 2007/0212704 A1 | 9/2007 | Dong et al. |
| 2007/0225487 A1 | 9/2007 | Nilsson et al. |
| 2007/0238122 A1 | 10/2007 | Allbritton et al. |
| 2007/0244675 A1 | 10/2007 | Shai et al. |
| 2007/0264653 A1 | 11/2007 | Berlin et al. |
| 2008/0003142 A1 | 1/2008 | Link et al. |
| 2008/0014589 A1 | 1/2008 | Link et al. |
| 2008/0076118 A1 | 3/2008 | Tooke et al. |
| 2008/0081330 A1 | 4/2008 | Kahvejian |
| 2008/0085836 A1 | 4/2008 | Kearns et al. |
| 2008/0090239 A1 | 4/2008 | Shoemaker et al. |
| 2008/0125324 A1 | 5/2008 | Petersdorf et al. |
| 2008/0176209 A1 | 7/2008 | Muller et al. |
| 2008/0269068 A1 | 10/2008 | Church et al. |
| 2008/0280955 A1 | 11/2008 | McCamish |
| 2008/0293589 A1 | 11/2008 | Shapero |
| 2009/0009904 A1 | 1/2009 | Yasuna et al. |
| 2009/0019156 A1 | 1/2009 | Mo et al. |
| 2009/0026082 A1 | 1/2009 | Rothberg et al. |
| 2009/0029385 A1 | 1/2009 | Christians et al. |
| 2009/0035777 A1* | 2/2009 | Kokoris ............ C12Q 1/6869 435/6.12 |
| 2009/0042206 A1 | 2/2009 | Schneider et al. |
| 2009/0098551 A1 | 4/2009 | Landers et al. |
| 2009/0099041 A1 | 4/2009 | Church et al. |
| 2009/0105081 A1 | 4/2009 | Rodesch et al. |
| 2009/0119313 A1 | 5/2009 | Pearce |
| 2009/0127589 A1 | 5/2009 | Rothberg et al. |
| 2009/0129647 A1 | 5/2009 | Dimitrova et al. |
| 2009/0156412 A1 | 6/2009 | Boyce, IV et al. |
| 2009/0163366 A1 | 6/2009 | Nickerson et al. |
| 2009/0181389 A1 | 7/2009 | Li et al. |
| 2009/0191565 A1 | 7/2009 | Lapidus et al. |
| 2009/0192047 A1 | 7/2009 | Parr et al. |
| 2009/0202984 A1 | 8/2009 | Cantor |
| 2009/0203014 A1 | 8/2009 | Wu et al. |
| 2009/0220955 A1 | 9/2009 | Verrant |
| 2009/0226975 A1 | 9/2009 | Sabot et al. |
| 2009/0233814 A1 | 9/2009 | Bashkirov et al. |
| 2009/0298064 A1 | 12/2009 | Batzoglou et al. |
| 2009/0301382 A1 | 12/2009 | Patel |
| 2009/0318310 A1 | 12/2009 | Liu et al. |
| 2010/0035243 A1 | 2/2010 | Muller et al. |
| 2010/0035252 A1 | 2/2010 | Rothberg et al. |
| 2010/0063742 A1 | 3/2010 | Hart et al. |
| 2010/0069263 A1 | 3/2010 | Shendure et al. |
| 2010/0076185 A1 | 3/2010 | Adey et al. |
| 2010/0086914 A1 | 4/2010 | Bentley et al. |
| 2010/0086926 A1 | 4/2010 | Craig et al. |
| 2010/0105107 A1 | 4/2010 | Hildebrand et al. |
| 2010/0137143 A1 | 6/2010 | Rothberg et al. |
| 2010/0137163 A1 | 6/2010 | Link et al. |
| 2010/0143908 A1 | 6/2010 | Gillevet |
| 2010/0159440 A1 | 6/2010 | Messier et al. |
| 2010/0188073 A1 | 7/2010 | Rothberg et al. |
| 2010/0196911 A1 | 8/2010 | Hoffman et al. |
| 2010/0197507 A1 | 8/2010 | Rothberg et al. |
| 2010/0216151 A1 | 8/2010 | Lapidus et al. |
| 2010/0216153 A1 | 8/2010 | Lapidus et al. |
| 2010/0227329 A1 | 9/2010 | Cuppens |
| 2010/0248984 A1 | 9/2010 | Shaffer et al. |
| 2010/0282617 A1 | 11/2010 | Rothberg et al. |
| 2010/0285578 A1 | 11/2010 | Selden et al. |
| 2010/0297626 A1 | 11/2010 | McKernan et al. |
| 2010/0300559 A1 | 12/2010 | Schultz et al. |
| 2010/0300895 A1 | 12/2010 | Nobile et al. |
| 2010/0301042 A1 | 12/2010 | Kahlert |
| 2010/0301398 A1 | 12/2010 | Rothberg et al. |
| 2010/0304982 A1 | 12/2010 | Hinz et al. |
| 2010/0311061 A1 | 12/2010 | Korlach et al. |
| 2010/0330619 A1 | 12/2010 | Willis et al. |
| 2011/0004413 A1 | 1/2011 | Carnevali et al. |
| 2011/0009278 A1 | 1/2011 | Kain et al. |
| 2011/0015863 A1 | 1/2011 | Pevzner et al. |
| 2011/0021366 A1 | 1/2011 | Chinitz et al. |

(56) References Cited

U.S. PATENT DOCUMENTS

| | | |
|---|---|---|
| 2011/0034342 A1 | 2/2011 | Fox |
| 2011/0092375 A1 | 4/2011 | Zamore et al. |
| 2011/0098193 A1 | 4/2011 | Kingsmore et al. |
| 2011/0117544 A1 | 5/2011 | Lexow |
| 2011/0159499 A1 | 6/2011 | Hindson et al. |
| 2011/0166029 A1 | 7/2011 | Margulies et al. |
| 2011/0224105 A1 | 9/2011 | Kum et al. |
| 2011/0230365 A1 | 9/2011 | Rohlfs et al. |
| 2011/0257889 A1 | 10/2011 | Klammer et al. |
| 2011/0288780 A1 | 11/2011 | Rabinowitz et al. |
| 2011/0301042 A1 | 12/2011 | Steinmann et al. |
| 2012/0015050 A1 | 1/2012 | Abkevich et al. |
| 2012/0021930 A1 | 1/2012 | Schoen et al. |
| 2012/0046877 A1 | 2/2012 | Hyland et al. |
| 2012/0059594 A1 | 3/2012 | Hatchwell et al. |
| 2012/0074925 A1 | 3/2012 | Oliver |
| 2012/0079980 A1 | 4/2012 | Taylor et al. |
| 2012/0115736 A1 | 5/2012 | Bjornson et al. |
| 2012/0164630 A1 | 6/2012 | Porreca et al. |
| 2012/0165202 A1 | 6/2012 | Porreca et al. |
| 2012/0179384 A1 | 7/2012 | Kuramitsu et al. |
| 2012/0214678 A1 | 8/2012 | Rava et al. |
| 2012/0216151 A1 | 8/2012 | Sarkar et al. |
| 2012/0236861 A1 | 9/2012 | Ganeshalingam et al. |
| 2012/0245041 A1 | 9/2012 | Brenner et al. |
| 2012/0252020 A1 | 10/2012 | Shuber |
| 2012/0252684 A1 | 10/2012 | Selifonov et al. |
| 2012/0258461 A1 | 10/2012 | Weisbart |
| 2012/0270212 A1 | 10/2012 | Rabinowitz et al. |
| 2012/0270739 A1 | 10/2012 | Rava et al. |
| 2013/0129755 A1 | 5/2013 | Song |
| 2013/0130921 A1 | 5/2013 | Gao et al. |
| 2013/0178378 A1 | 7/2013 | Hatch et al. |
| 2013/0183672 A1 | 7/2013 | de Laat et al. |
| 2013/0222388 A1 | 8/2013 | McDonald |
| 2013/0268206 A1 | 10/2013 | Porreca et al. |
| 2013/0268474 A1 | 10/2013 | Nizzari et al. |
| 2013/0274146 A1 | 10/2013 | Umbarger et al. |
| 2013/0275103 A1 | 10/2013 | Struble et al. |
| 2013/0288242 A1 | 10/2013 | Stoughton et al. |
| 2013/0323730 A1 | 12/2013 | Curry et al. |
| 2013/0332081 A1 | 12/2013 | Reese et al. |
| 2013/0337447 A1 | 12/2013 | Porreca et al. |
| 2013/0344096 A1 | 12/2013 | Chiang et al. |
| 2014/0129201 A1 | 5/2014 | Kennedy et al. |
| 2014/0136120 A1 | 5/2014 | Colwell et al. |
| 2014/0206552 A1 | 7/2014 | Rabinowitz et al. |
| 2014/0222349 A1 | 8/2014 | Higgins et al. |
| 2014/0228226 A1 | 8/2014 | Yin et al. |
| 2014/0255931 A1 | 9/2014 | Porreca et al. |
| 2014/0274741 A1 | 9/2014 | Hunter et al. |
| 2014/0308667 A1 | 10/2014 | Umbarger |
| 2014/0318274 A1 | 10/2014 | Zimmerman et al. |
| 2014/0342354 A1 | 11/2014 | Evans et al. |
| 2014/0342940 A1 | 11/2014 | Oliphant et al. |
| 2014/0361022 A1 | 12/2014 | Finneran |
| 2015/0051085 A1 | 2/2015 | Vogelstein et al. |
| 2015/0056613 A1 | 2/2015 | Kural |
| 2015/0111208 A1 | 4/2015 | Umbarger et al. |
| 2015/0178445 A1 | 6/2015 | Cibulskis et al. |
| 2015/0258170 A1 | 9/2015 | McCabe et al. |
| 2015/0299767 A1 | 10/2015 | Armour et al. |
| 2015/0310163 A1 | 10/2015 | Kingsmore et al. |
| 2015/0354003 A1 | 12/2015 | Umbarger |
| 2016/0003812 A1 | 1/2016 | Porreca et al. |
| 2016/0034638 A1 | 2/2016 | Spence et al. |
| 2016/0068889 A1 | 3/2016 | Gole et al. |
| 2016/0188793 A1 | 6/2016 | Muzzey et al. |
| 2016/0210486 A1 | 7/2016 | Porreca et al. |
| 2016/0251719 A1 | 9/2016 | Umbarger |
| 2017/0044610 A1 | 2/2017 | Johnson |
| 2017/0129964 A1 | 5/2017 | Cheung |
| 2017/0183731 A1* | 6/2017 | Mann ............... G16B 30/00 |
| 2017/0275676 A1 | 9/2017 | Umbarger |
| 2018/0371533 A1 | 12/2018 | Gore et al. |
| 2019/0233881 A1 | 8/2019 | Umbarger et al. |
| 2020/0181696 A1 | 6/2020 | Porreca et al. |

FOREIGN PATENT DOCUMENTS

| | | |
|---|---|---|
| EP | 2425240 A2 | 3/2012 |
| EP | 2 437 191 A2 | 4/2012 |
| EP | 2716766 A1 | 4/2014 |
| WO | 95/011995 A1 | 5/1995 |
| WO | 96/019586 A1 | 6/1996 |
| WO | 98/014275 A1 | 4/1998 |
| WO | 98/044151 A1 | 10/1998 |
| WO | 00/018957 A1 | 4/2000 |
| WO | 02/093453 A2 | 11/2002 |
| WO | 2004/018497 A2 | 3/2004 |
| WO | 2004/083819 A2 | 9/2004 |
| WO | 2005/003304 A2 | 1/2005 |
| WO | 2006/084132 A2 | 8/2006 |
| WO | 2007/010251 A2 | 1/2007 |
| WO | 2007/061284 A1 | 5/2007 |
| WO | 2007/107717 A1 | 9/2007 |
| WO | 2007/123744 A2 | 11/2007 |
| WO | 2007/135368 A2 | 11/2007 |
| WO | 2008067551 A2 | 6/2008 |
| WO | 2009/036525 A2 | 3/2009 |
| WO | 2009/076238 A2 | 6/2009 |
| WO | 2010/024894 A1 | 3/2010 |
| WO | 2010/115154 A1 | 10/2010 |
| WO | 2010/126614 A2 | 11/2010 |
| WO | 2011/006020 A1 | 1/2011 |
| WO | 2011066476 A1 | 6/2011 |
| WO | 2011067378 A1 | 6/2011 |
| WO | 2011/102998 A2 | 8/2011 |
| WO | 2011/155833 A2 | 12/2011 |
| WO | 2012/006291 A2 | 1/2012 |
| WO | 2012/040387 A1 | 3/2012 |
| WO | 2012/051208 A2 | 4/2012 |
| WO | 2012/087736 A1 | 6/2012 |
| WO | 2012/109500 A2 | 8/2012 |
| WO | 2012/134884 A1 | 10/2012 |
| WO | 2012/149171 A1 | 11/2012 |
| WO | 2012/170725 A2 | 12/2012 |
| WO | 2013/058907 A1 | 4/2013 |
| WO | 2013/148496 A1 | 10/2013 |
| WO | 2013/177086 A1 | 11/2013 |
| WO | 2013/191775 A2 | 12/2013 |
| WO | 2014/052909 A2 | 4/2014 |
| WO | 2014/074246 A1 | 5/2014 |
| WO | 2015/119941 A2 | 8/2015 |

OTHER PUBLICATIONS

Di Gusto et al., Nucleic Acids Research 31(3): e7 (Year: 2003).*
Eckstein, F. Antisense &Nucleic acid Drug Development 10 :117-121 (Year: 2000).*
Sayers et al.,Nucleic Acids Research 16(3) :791-802 (Year: 1988).*
Sayers et al., JBC 265(30): 18311-18317 (Year: 1990).*
Zhu et al., New J. Chem. 37:927 (Year: 2013).*
Schouten et al. Nucleic Acids Research 30(12) : e57 (Year: 2002).*
Skerra, Nucleic Acids Research 20(14): 3551-3554 (Year: 1992).*
Brown et al.;. J.of Biological Chemistry 269(43) :26801 (Year: 1994).*
Ageno, 1969, The alkaline denaturation of DNA, Biophys J 9(11):1281-1311.
Akhras, 2007, Connector Inversion Probe Technology: A Powerful OnePrimer Multiplex DNA Amplification System for Numerous Scientific Applications Plos One 2(9):e915.
Alazard, 2006, Sequencing oligonucleotides by enrichment of coupling failures using matrix-assisted laser desorption/ionization time-of-flight mass spectrometry, Curr Protoc Nucleic Acid Chem, Chapter 10, Unit 10:1-7.
Alazard, 2002, Sequencing of production-scale synthetic oligonucleotides by enriching for coupling failures using matrix-assisted laser desorption/ionization time-of-flight mass spectrometry, Anal Biochem 301:57-64.

(56) References Cited

OTHER PUBLICATIONS

Albert, 2007, Direct selection of human genomic loci by microarray hybridization, Nature Methods 4(11):903-5.
Aljanabi, 1997, Universal and rapid salt-extraction of high quality genomic DNA for PCR-based techniques, Nucl. Acids Res 25:4692 4693.
Antonarakis and the Nomenclature Working Group, 1998, Recommendations for a nomenclature system for human gene mutations, Human Mutation 11:1-3.
Australian Patent Examination Report No. 1 dated Aug. 12, 2014, for Australian Patent Application No. 2010242073, filed Apr. 30, 2010, (4 pages).
Ball, 2009, Targeted and genome-scale strategies reveal gene-body methylation signatures in human cells, Nat Biotech 27:361-8.
Balzer, 2013, Filtering duplicate reads from 454 pyrosequencing data, Bioinformatics 29(7):830-836.
Barany, 1991, Genetic disease detection and DNA amplification using cloned thermostable ligase, PNAS 88:189-193.
Barany, 1991, The Ligase Chain Reaction in a PCR World, Genome Research 1:5-16.
Bau, 2008, Targeted next-generation sequencing by specific capture of multiple genomic loci using low-volume microfluidic DNA arrays, Analytical and Bioanal Chem 393(1):171-5.
Beer, 1962, Determination of base sequence in nucleic acids with the electron microscope: visibility of a marker, PNAS 48(3):409-416.
Bell, 2011, Carrier testing for severe childhood recessive diseases by next-generation sequencing, Sci Trans Med 3 (65ra4).
Benner, 2001, Evolution, language and analogy in functional genomics, Trends Genet 17:414-8.
Bentzley, 1996, Oligonucleotide sequence and composition determined by matrix-assisted laser desorption/ionization, Anal Chem 68:2141-2146.
Bentzley, 1998, Base specificity of oligonucleotide digestion by calf spleen phosphodiesterase with matrix-assisted laser desorption ionization analysis, Anal Biochem 258:31-37.
Bickle, 1993, Biology of DNA Restriction, Microbiol Rev 57(2):434-50.
Bonfield, 2013, Compression of FASTQ and SAM format sequencing data, PLoS One 8(3):e59190.
Bose, 2012, BIND—An algorithm for loss-less compression of nucleotide sequence data, J Biosci 37(4):785-789.
Boyden, 2013, High-throughput screening for SMN1 copy number loss by next-generation sequencing, American Society of Human Genetics 63rd Annual Meeting, Abstract, Oct. 22, 2013.
Boyer, 1971, DNA restriction and modification mechanisms in bacteria, Ann Rev Microbiol 25:153-76.
Braasch, 2001, Locked nucleic acid (LNA): fine-tuning the recognition of DNA and RNA, Chemistry & Biology 8(1):1-7.
Braslavsky, 2003, Sequence information can be obtained from single DNA molecules, PNAS 100:3960-4.
Brown et al., 1979, Chemical synthesis and cloning of a tyrosine tRNA gene, Methods Enzymol 68:109-51.
Browne, 2002, Metal ion-catalyzed nucleic Acid alkylation and fragmentation, J Am Chem Soc 124(27):7950-7962.
Brownstein, 2014, An international effort towards developing standards for best practices in analysis, interpretation and reporting of clinical genome sequencing results in the Clarity Challenge, Genome Biol 15:R53.
Bunyan, 2004, Dosage analysis of cancer predisposition genes by multiplex ligation-dependent probe amplification, British Journal of Cancer, 91(6):1155-59.
Burrow, 1994, A block-sorting lossless data compression algorithm, Technical Report 124, Digital Equipment Corporation, CA.
Castellani, 2008, Consenses on the use of and interpretation of cystic fibrosis mutation analysis in clinical practice, J Cyst Fib 7:179-196.
Challis, 2012, An integrative variant analysis suite for whole exome next-generation sequencing data, BMC Informatics 13(8):1-12.

Chan, 2011, Natural and engineered nicking endonucleases—from cleavage mechanism to engineering of strand-specificity, Nucl Acids Res 39(1):1-18.
Chennagiri, 2013, A generalized scalable database model for storing and exploring genetic variations detected using sequencing data, American Society of Human Genetics 63rd Annual Meeting, Abstract, Oct. 22, 2013.
Chevreux, 1999, Genome sequence assembly using trace signals and additional sequence information, Proc GCB 99:45-56.
Chirgwin et al., 1979, Isolation of biologically active ribonucleic acid from sources enriched in ribonuclease, Biochemistry, 18:5294-99.
Choe, 2010, Novel CFTR Mutations in a Korean Infant with Cystic Fibrosis and Pancreatic Insufficiency, J Korean Med Sci 25:163-5.
Ciotti, 2004, Triplet repeat prmied PCR (TP PCR) in molecular diagnostic testing for Friedrich ataxia, J Mol Diag 6(4):285-9.
Cock, 2010, The Sanger FASTQ file format for sequences with quality scores, and the Solexa/Illumina FASTQ variants. Nucleic Acids Res 38(6):1767-1771.
Collins, 2004, Finishing the euchromatic sequence of the human genome, Nature 431(7011):931-45.
Dahl et al., 2005, Multiplex amplification enabled by selective circularization of large sets of genomic DNA fragments, Nucleic Acids Res 33(8):e71.
Danecek, 2011, The variant call format and VCFtools, Bioinformatics 27(15):2156-2158.
De la Bastide, 2007, Assembling genome DNA sequences with PHRAP, Current Protocols in Bioinformatics 17:11.4.1-11.4.15.
Delcher, 1999, Alignment of whole genomes, Nuc Acids Res 27(11):2369-2376.
Den Dunnen, 2003, Mutation Nomenclature, Curr Prot Hum Genet 7.13.1-7.13.8.
Deng, 2009, Targeted bisulfite sequencing reveals changes in DNA methylation associated with nuclear reprogramming, nature biotechnology 27:353-60 (and supplement).
Deng et. al., 2012, Supplementary Material, Nature Biotechnology, S1-1-S1-1 1, Retrieved from the Internet on Oct. 24, 2012.
Diguistini, 2009, De novo sequence assembly of a filamentous fungus using Sanger, 454 and Illumina sequence data, Genome Biology, 10:R94.
Dong & Yu, 2011, Mutation surveyor: An in silico tool for sequencing analysis, Methods Mol Biol 760:223-37.
Dudley, 2009, A quick guide for developing effective bioinformatics programming skills, PLoS Comp Biol 5(12):e1000589.
Moudrianakis, 1965, Base Sequence Determination in Nucleic Acids with the Electron Microscope, III. Chemistry and Microscopy of Guanine-Labeled DNA, PNAS, 53:564-71.
Mullan, 2002, Multiple sequence alignment-the gateway to further analysis, Brief Bioinform 3(3):303-5.
Nan, 2006, A novel CFTR mutation found in a Chinese patient with cystic fibrosis, Chinese Med J 119(2):103-9.
Narang, 1979, Improved phosphotriester method for the synthesis of gene fragments, Meth Enz 68:90-98.
Ng, 2009, Targeted capture and massively parallel sequencing of 12 human exomes, Nature 461(7261):272-6.
Nicholas, 2002, Strategies for multiple sequence alignment, Biotechniques 32:572-91.
Nickerson, 1990, Automated DNA diagnostics using an ELISA-based oligonucleotide ligation assay, PNAS 87:8923-7.
Nielsen et al., 1999, Peptide Nucleic Acids, Protocols and Applications (Norfolk: Horizon Scientific Press, 1-19).
Nilsson, 2006, Analyzing genes using closing and replicating circles, Trends in Biotechnology 24:83-8.
Ning, 2001, SSAHA: a fast search method for large DNA databases, Genome Res 11(10):1725-9.
Nordhoff, 1993, Ion stability of nucleic acids in infrared matrix-assisted laser desorption/ ionization mass spectrometry, Nucl Acid Res 21(15):3347-57.
Nuttle, 2013, Rapid and accurate large-scale genotyping of duplicated genes and discovery of interlocus gene conversions, Nat Meth 10(9):903-909.

(56) References Cited

OTHER PUBLICATIONS

Nuttle, 2014, Resolving genomic disorder-associated breakpoints within segmental DNA duplications using massively parallel sequencing, Nat Prot 9(6):1496-1513.
Oefner, 1996, Efficient random sub-cloning of DNA sheared in a recirculating point-sink flow system, Nucleic Acids Res 24(20):3879-3886.
Oka, 2006, Detection of loss of heterozygosity in the p53 gene in renal cell carcinoma and bladder cancer using the polymerase chain reaction, Mol Carcinogenesis 4(1):10-13.
Okoniewski, 2013, Precise breakpoint localization of large genomic deletions using PacBio and Illumina next-generation sequencers, Biotechniques 54(2):98-100.
Oliphant, 2002, BeadArray technology: enabling an accurate, cost-effective approach to high-throughput genotyping, Biotechniques Suppl:56-8, 60-1.
Ordahl, 1976, Sheared DNA fragment sizing: comparison of techniques, Nucleic Acids Res 3:2985-2999.
Ostrer, 2001, A genetic profile of contemporary Jewish populations, Nat Rev Genet 2(11):891-8.
Owens, 1998, Aspects of oligonucleotide and peptide sequencing with MALDI and electrospray mass spectrometry, Bioorg Med Chem 6:1547-1554.
Parameswaran, 2007, A pyrosequencing-tailored nucleotide barcode design unveils opportunities for large-scale sample multiplexing, Nucl Acids Rese 35:e130.
Pastor, 2010, Conceptual modeling of human genome mutations: a dichotomy between what we have and what we shoudl have, 2010 Proc BIOSTEC Bioinformatics, pp. 160-166.
Paton, 2000, Conceptual modelling of genomic information, Bioinformatics 16(6):548-57.
Pearson, 1988, Improved tools for biological sequence comparison, PNAS 85(8):2444-8.
Pertea, 2003, TIGR gene indices clustering tools (TGICL), Bioinformatics 19(5):651-52.
Pieles, 1993, Matrix-assisted laser desorption ionization time-of-flight mass spectrometry: A powerful tool for the mass and sequence analysis of natural and modified oligonucleotides, Nucleic Acids Res 21:3191-3196.
Pinho, 2013, MFCompress: a compression tool for FASTA and multi-FASTA data, Bioinformatics 30(1):117-8.
Porreca, 2007, Multiplex amplification of large sets of human exons, Nat Meth 4(11):931-936.
Porreca, 2013, Analytical performance of a Next-Generation DNA sequencing-based clinical workflow for genetic carrier screening, American Society of Human Genetics 63rd Annual Meeting, Abstract, Oct. 22, 2013.
Procter, 2006, Molecular diagnosis of Prader-Willi and Angelman syndromes by methylation-specific melting analysis and methylation-specific multiplex ligation-dependent probe amplification, Clin Chem 52(7):1276-83.
Quail, 2010, DNA: Mechanical Breakage, In Encyclopedia of Life Sciences, John Wiley & Sons Ltd, Chicester (5 pages).
Rambaut, 1997, Seq-Gen:an application for the Monte Carlo simulation of DNA sequence evolution along phylogenetic trees, Bioinformatics 13:235-38.
Richards, 2008 ACMG recommendations for standards for interpretation and reporting of sequence variations: Revisions, Genet Med 10(4):294-300.
Richter, 2008, MetaSim—A Sequencing Simulator for Genomics and Metagenomics, PLoS One 3:e3373.
Roberts, 1980, Restriction and modification enzymes and their recognition sequences, Nucleic Acids Res 8(1):r63-r80.
Rodriguez, 2010, Constructions from Dots and Lines, Bull Am Soc Inf Sci Tech 36(6):35-41.
Rosendahl et al., 2013, CFTR, SPINK1, CTRC and PRSS1 variants in chronic pancreatitis: is the role of mutated CFTR overestimated?, Gut 62:582-592.
Rothberg, 2011, An integrated semiconductor device enabling non-optical genome sequencing, Nature 475:348-352.
Rowntree, 2003, The phenotypic consequences of CFTR mutations, Ann Hum Gen 67:471-485.
Sanger, 1977, DNA Sequencing with chain-terminating inhibitors, PNAS 74(12):5463-5467.
Santa Lucia, 1998, A unified view of polymer, dumbbell, and oligonucleotide DNA nearest-neighbor thermodynamics, PNAS 95(4):1460-5.
Sargent, 1988, Isolation of differentially expressed genes, Methods Enzymol 152:423-432.
Sauro, 2004, How Do You Calculate a Z-Score/ Sigma Level?, https://www.measuringusability.com/zcalc.htm (online publication).
Sauro, 2004, What's a Z-Score and Why Use it in Usability Testing?, https://www.measuringusability.com/z.htm (online publication).
Schadt, 2010, A window into third-generation sequencing, Human Mol Genet 19(R2):R227-40.
Schatz et al., 2010, Assembly of large genomes using second-generation sequencing, Genome Res., 20:1165-1173.
Schiffman, 2009, Molecular inversion probes reveal patterns of 9p21 deletion and copy number aberrations in childhood leukemia, Cancer Genetics and Cytogenetics 193:9-18.
Schneeberger, 2011, Reference-guided assembly of four diverse *Arabidopsis thaliana* genomes, PNAS 108(25):10249-10254.
Schrijver, 2005, Diagnostic testing by CTFR gene mutation analysis in a large group of Hispanics, J Mol Diag 7(2):289-299.
Examination Report from the European Patent Office for EP 10770071.8 dated Jul. 16, 2013, (5 pages).
Extended European Search Report for Application No. 12765217.0 dated Aug. 26, 2014, (5 pages).
Extended European Search Report dated Nov. 11, 2015, for EP Application 13772357.3 (8 pages).
Fares, 2008, Carrier frequency of autosomal-recessive disorders in the Ashkenazi Jewish population: should the rationale for mutation choice for screening be reevaluated?, Prenatal Diagnosis 28:236-41.
Faulstich, 1997, A sequencing method for RNA oligonucleotides based on mass spectrometry, Anal Chem 69:4349-4353.
Faust, 2014, Samblaster: fast duplicate marking and structural variant read extraction, Bioinformatics published online May 7, 2014.
Fitch, 1970, Distinguishing homologs from analogous proteins, Syst Biol 19(2):99-113.
Frey, 2006, Statistics Hacks 108-115.
Friedenson, 2005, BRCA1 and BRCA2 Pathways and the Risk of Cancers Other Than Breast or Ovarian, Medscape General Medicine 7(2):60.
Furtado, 2011, Characterization of large genomic deletions in the FBN1 gene using multiplex ligation-dependent probe amplification, BMC Med Gen 12:119-125.
Garber, 2008, Fixing the front end, Nat Biotech 26(10):1101-1104.
Gemayel, 2010, Variable tandem repeats accelerate evolution of coding and regulatory sequences, Ann Rev Genet 44:445-77.
Glover, 1995, Sequencing of oligonucleotides using high performance liquid chromatography and electrospray mass spectrometry, Rapid Com Mass Spec 9:897-901.
Gnirke et al., 2009, Solution hybrid selection with ultra-long oligonucleotides for massively parallel targeted sequencing, nature biotechnology 27:182-9.
Goto, 2010, BioRuby: bioinformatics software for the Ruby programming language, Bioinformatics 26(20):2617-2619.
Goto, 1994, A Study on Development of a Deductive Object-Oriented Database and Its Application to Genome Analysis, PhD Thesis, Kyushu University, Kyushu, Japan (106 pages).
Guerrero-Fernandez, 2013, FQbin: a compatible and optimize dformat for storing and managing sequence data, IWBBIO Proceedings, Granada 337-344.
Gustincich et al., 1991, A fast method for high-quality genomic DNA extraction from whole human blood, BioTechniques 11(3):298-302.
Gut, 2995, A procedure for selective DNA alkylation and detection by mass spectrometry, Nucl Acids Res 23(8):1367-1373.

(56) References Cited

OTHER PUBLICATIONS

Hallam, 2014, Validation for Clinical Use of, and Initial Clinical Experience with, a Novel Approach to Population-Based Carrier Screening using High-Throughput Next-Generation DNA Sequencing, J Mol Diagn 16:180-9.
Hammond, 1996, Extraction of DNA from preserved animal specimens for use in randomly amplified polymorphic DNA analysis, Anal Biochem 240:298-300.
Hardenbol, 2003, Multiplexed genotyping with sequence-tagged molecular inversion probes, Nat Biotech 21:673-8.
Hardenbol, 2005, Highly multiplexed molecular inversion probe genotyping: over 10,000 targeted SNPs genotyped in a single tube assay, Genome Res 15:269-75.
Harris, 2006, Defects can increase the melting temperature of DNA-nanoparticle assemblies, J Phys Chem B 110(33):16393-6.
Harris, 2008, Single-molecule DNA sequencing of a viral genome, Science 320(5872):106-9.
Hiatt, 2013, Single molecule molecular inversion probes for targeted, high-accuracy detection of low-frequency variation. Genome Res 23:843-54.
Hodges, 2007, Genome-wide in situ exon capture for selective resequencing, Nat Genet 39(12):1522-7.
Holland, 2008, BioJava: an open-source framework for bioinformatics, Bioinformatics 24(18):2096-2097.
Homer, 2009, BFAST: An alignment tool for large scale genome resequencing, PLoS One 4(11):e7767.
Huang, 2008, Comparative analysis of common CTFR polymorphisms poly-T, TGrepeats and M470V in a healthy Chinese population, World J Gastroenterol 14(12):1925-30.
Husemann, 2009, Phylogenetic Comparative Assembly, Algorithms in Bioinformatics: 9th International Workshop, pp. 145-156, Salzberg & Warnow, Eds. Springer-Verlag, Berlin, Heidelberg.
Illumina, 2010, De Novo assembly using Illumina reads, Technical Note (8 pages).
International Search Report and Written Opinion dated Feb. 4, 2014, for Patent Application No. PCT/US13/62842, filed Oct. 1, 2013.
International Search Report and Written Opinion for PCT/US13/61691 dated Jan. 10, 2014 (10 pages).
International Search Report and Written Opinion dated Jun. 10, 2013 for related application PCT/US13/33435 with an International filing date of Mar. 22, 2013 (7 pages).
International Search Report and Written Opinion dated Apr. 3, 2012, for International Patent Application No. PCT/US2011/065098, filed Dec. 15, 2011 (8 pages).
International Search Report and Written Opinion dated Aug. 12, 2013, for International Patent Application No. PCT/US13/36575, filed Apr. 15, 2013 (9 pages).
International Search Report and Written Opinion dated Dec. 9, 2014, for International Patent Application No. PCT/US14/28212, filed Mar. 14, 2014 (11 pages).
International Search Report and Written Opinion dated Feb. 25, 2013 for International Patent Application No. PCT/US12/55362.
International Search Report and Written Opinion dated Oct. 28, 2010, for Patent Application No. PCT/US2010/001293, filed Apr. 30, 2010 (8 pages).
International Search Report and Written Opinion dated Jan. 7, 2015, for International Patent Application No. PCT/US14/60256, filed Oct. 13, 2014 (9 pages).
International Search Report and Written Opinion dated Jun. 10, 2013, for International Patent Application No. PCT/US13/33435, filed Mar. 22, 2013 (6 pages).
International Search Report and Written Opinion dated Jun. 14, 2012, for International Patent Application No. PCT/US12/29790, filed Mar. 20, 2012 (8 pages).
International Search Report and Written Opinion dated Jun. 28, 2013, for Patent Application No. PCT/US2013/032885, filed Mar. 19, 2013 (9 pages).
International Search Report and Written Opinion dated May 4, 2016, for International patent application No. PCT/US2016/012886 with international filing date Jan. 6, 2015 (7 pages).
International Search Report and Written Opinion dated Nov. 1, 2013, for International Patent Application No. PCT/US2013/044039, filed Jun. 4, 2013 (6 pages).
International Search Report and Written Opinion dated Jan. 29, 2015, for Patent Application No. PCT/US14/61138, filed Oct. 17, 2014, (11 pages).
International Search Report and Written Opinion dated Jan. 29, 2015, for Patent Application No. PCT/US2014/060056, filed Oct. 10, 2014, (14 pages).
International Search Report and Written Opinion dated Sep. 3, 2014 for International Patent Application No. PCT/US14/27324, filed Mar. 14, 2014, (8 pages).
Iqbal, 2012, De novo assembly and genotyping of variants using colored de Bruijn graphs, Nature Genetics 44:226-232.
Jaijo, 2010, Microarray-based mutation analysis of 183 Spanish families with Usher syndrome, Invest Ophthalmol Vis Sci 51(3):1311-7.
Jensen, 2001, Orthologs and paralogs—we need to get it right, Genome Biol 2(8):1002-1002.3.
Jones, 2008, Core signaling pathways in human pancreatic cancers revealed by global genomic analyses, Science 321(5897):1801-1806.
Kennedy et al., 2013, Accessing more human genetic variation with short sequencing reads, American Society of Human Genetics 63rd Annual Meeting, Abstract, Oct. 22, 2013.
Kent, 2002, BLAT-The BLAST-like alignment tool, Genome Res 12(4): 656-664.
Kircher, 2010, High-throuhgput DNA sequencing—concepts and limitations, Bioassays 32:524-36.
Kirpekar, 1994, Matrix assisted laser desorption/ionization mass spectrometry of enzymatically synthesized RNA up to 150 kDa, Nucl Acids Res 22:3866-3870.
Klein, 2011, LOCAS—A low coverage sequence assembly tool for re-sequencing projects, PLoS One 6(8):e23455.
Kneen, 1998, Green fluorescent protein as a noninvasive intracellular pH indicator, Biophys J 74(3):1591-99.
Koboldt, 2009, VarScan: variant detection in massively parallel sequencing of individual and pooled samples, Bioinformatics 25:2283-85.
Krawitz, 2010, Microindel detection in short-read sequence data, Bioinformatics 26(6):722-729.
Kreindler, 2010, Cystic fibrosis: exploiting its genetic basis in the hunt for new therapies, Pharmacol Ther 125(2):219-229.
Krishnakumar, 2008, A comprehensive assay for targeted multiplex amplification of human DNA sequences, PNAS 105:9296-301.
Kumar, 2010, Comparing de novo assemblers for 454 transcriptome data, Genomics 11:571.
Kurtz, 2004, Versatile and open software for comparing large genomes, Genome Biol 5:R12.
Lam, 2008, Compressed indexing and local alignment of DNA, Bioinformatics 24(6):791-97.
Langmead, 2009, Ultrafast and memory-efficient alignment of short DNA sequences to the human genome, Genome Biol 10:R25.
Larkin, 2007, Clustal W and Clustal X version 2.0, Bioinformatics, 23(21):2947-2948.
Lecompte, 2001, Multiple alignment of complete sequences (MACS) in the post-genomic era, Gene 270(1-2):17-30.
Li, 2009, Fast and accurate short read alignment with Burrows-Wheeler transform, Bioinformatics, 25(14):1754-60.
Li, 2010, Fast and accurate long-read alignment with Burrows-Wheeler transform, Bioinformatics 26(5):589-95.
Li, 2012, A new approach to detecting low-level mutations in next-generation sequence data, Genome Biol 13:1-15.
Li, 2008, SOAP: short oligonucleotide alignment program, Bioinformatics 24(5):713-14.
Li, 2011, Single nucleotide polymorphism genotyping and point mutation detection by ligation on microarrays, J Nanosci Nanotechnol 11(2):994-1003.
Li, 2014, HUGO: Hierarchical mUlti-reference Genome compression for aligned reads, JAMIA 21:363-373.
Li, 2009, SOAP2: an improved ultrafast tool for short read alignment, Bioinformatics 25(15):1966-67.

(56) References Cited

OTHER PUBLICATIONS

Li, 2009, The Sequence Alignment/Map format and SAMtools, Bioinformatics 25(16):2078-9.
Lin, 2008, ZOOM! Zillions Of Oligos Mapped, Bioinformatics 24:2431.
Lin, 2010, A molecular inversion prove assay for detecting alternative splicing, BMC Genomics 11(712):1-14.
Lin, 2012, Development and evaluation of a reverse dot blot assay for the simultaneous detection of common alpha and beta thalassemia in Chinese, Blood Cells Molecules, and Diseases 48(2):86-90.
Lipman, 1985, Rapid and sensitive protein similarity searches, Science 227(4693):1435-41.
Liu, 2012, Comparison of next-generation sequencing systems, J Biomed Biotech 2012:251364.
Llopis, 1998, Measurement of cytosolic, mitochondrial, and Golgi pH in single living cells with green fluorescent proteins, PNAS 95(12):6803-08.
MacArthur, 2014, Guidelines for investigating causality of sequence variants in human disease, Nature 508:469-76.
Maddalena, 2005, Technical standards and guidelines: molecular genetic testing for ultra-rare disorders, Genet Med 7:571-83.
Malewicz, 2010, Pregel: a system for large-scale graph processing, Proc. ACM SIGMOD Int Conf Mgmt Data 135-46.
Mamanova, 2010, Target-enrichment sliategies for nextgeneration sequencing, Nature Methods 7(2):111-8.
Margulies, 2005, Genome sequencing in micro-fabricated high-density picotiter reactors, Nature, 437:376-380.
Marras, 1999, Multiplex detection of single-nucleotide variations using molecular beacons, Genetic Analysis Biomolecular Engineering 14:151.
Maxam, 1977, A new method for sequencing DNA, PNAS, 74:560 564.
May 1988, How Many Species Are There on Earth?, Science 241(4872):1441-9.
McKenna, 2010, The Genome Analysis Toolkit: a MapReduce framework for analyzing next-generation DNA sequencing data. Genome Res 20(9):1297-1303.
Meyer, 2008, Parallel tagged sequencing on the 454 platform, Nature Protocols 3(2):267-78.
Mills, 2010, Mapping copy number variation by population-scale genome sequencing, Nature 470(7332):59-65.
Minton, 2011, Mutation Surveyor: software for DNA sequence analysis, Meth Mol Biol 688:143-53.
Miyazaki, 2009, Characterization of deletion breakpoints in patients with dystrophinopathy carrying a deletion of exons 45-55 of the Duchenne muscular dystrophy (DMD) gene, J Hum Gen 54:127-30.
Mockler, 2005, Applications of DNA tiling arrays for whole-genome analysis, Genomics 85(1):1-15.
Mohammed, 2012, Deliminate—a fast and efficient methods for loss-less compression of genomice sequences, Bioinformatics 28(19):2527-2529.
Schuette, 1995, Sequence analysis of phosphorothioate oligonucleotides via matrix-assisted laser desorption ionization time-of-flight mass spectrometry, J Pharm Biomed Anal 13:1195-1203.
Schwartz, 2009, Identification of cystic fibrosis variants by polymerase chain reaction/oligonucleotide ligation assay, J Mol Diag 11(3):211-15.
Schwartz, 2011, Clinical utility of single nucleotide polymorphism arrays, Clin Lab Med 31(4):581-94.
Sequeira, 1997, Implementing generic, object-oriented models in biology, Ecological Modeling 94.1:17-31.
Shen, 2013, Multiplex capture with double-stranded DNA probes, Genome Medicine 5(50):1-8.
Sievers, 2011, Fast, scalable generation of high-quality protein multiple sequence alignments using Clustal Omega, Mol Syst Biol 7:539.
Simpson, 2009, ABySS: A parallel assembler for short read sequence data, Genome Res., 19(6):1117-23.
Slater, 2005, Automated generation of heuristics for biological sequence comparison, BMC Bioinformatics 6:31.
Smirnov, 1996, Sequencing oligonucleotides by exonuclease digestion and delayed extraction matrix-assisted laser desorption ionization time-of-flight mass spectrometry, Anal Biochem 238:19-25.
Soni, 2007, Progress toward ultrafast DNA sequencing using solid-state nanopores, Clin Chem 53(11):1996-2001.
Spanu, 2010, Genome expansion and gene loss in powdery mildew fungi reveal tradeoffs in extreme parasitism, Science 330(6010):1543-46.
Strom, 2005, Mutation detection, interpretation, and applications in the clinical laboratory setting, Mutat Res 573:160-67.
Summerer, 2009, Enabling technologies of genomic-scale sequence enrichment for targeted high-throughput sequencing, Genomics 94(6):363-8.
Sunnucks, 1996, Microsatellite and chromosome evolution of parthenogenetic sitobion aphids in Australia, Genetics 144:747-756.
Supplementary European Search Report for EP Application No. 10770071.8 dated Nov. 8, 2012, 17 pages.
Supplementary European Search Report dated Aug. 26, 2014, for European Patent Application No. 12765217.0, filed Mar. 20, 2012, (5 pages).
Supplementary European Search Report dated Oct. 26, 2015, for European patent application 13776268.8, being a regional stage entry of International Application No. PCT/US2013/032885 with International Filing Date Mar. 19, 2013 (7 pages).
Thauvin-Robinet, 2009, The very low penetrance of cystic fibrosis for the R117H mutation: a reappraisal for genetic counseling and newborn screening, J Med Genet 46:752-758.
Thiyagarajan, 2006, PathogenMIPer: a tool for the design of molecular inversion probes to detect multiple pathogens, BMC Bioinformatics 7:500.
Thompson, 1994, Clustal W: improving the sensitivity of progressive mulitple sequence alignment through sequence weighting, position-specific gap penalties and weight matrix choice, Nuc Acids Res 22:4673-80.
Thompson, 2011, The properties and applications of single-molecule DNA sequencing, Genome Biol 12(2):217.
Thorstenson, 1998, An Automated Hydrodynamic Process for Controlled, Unbiased DNA Shearing, Genome Res 8(8):848-855.
Thorvaldsdottir, 2012, Integrative Genomics Viewer (IGV): high-performance genomics data visualization and exploration, Brief Bioinform 24(2):178-92.
Tokino, 1996, Characterization of the human p57 KIP2 gene: alternative splicing, insertion/deletion polymorphisms in VNTR sequences in the coding region, and mutational analysis, Human Genetics 96:625-31.
Turner, 2009, Massively parallel exon capture and library-free resequencing across 16 genomes, Nat Meth 6:315-316.
Turner, 2009, Methods for genomic partitioning, Ann Rev Hum Gen 10:263-284.
Umbarger, 2013, Detecting contamination in Next Generation DNA sequencing libraries, American Society of Human Genetics 63rd Annual Meeting, Abstract, Oct. 22, 2013.
Umbarger, 2014, Next-generation carrier screening, Gen Med 16(2):132-140.
Veeneman, 2012, Oculus: faster sequence alignment by streaming read compression, BMC Bioinformatics 13:297.
Wallace, 1987, Oligonucleotide probes for the screening of recombinant DNA libraries, Meth Enz 152:432-442.
Wallace, 1979, Hybridization of synthetic oligodeoxyribonucteotides to dp x 174DNA:the effect of single base pair mismatch, Nucl Acids Res 6:3543-3557.
Wang et al., 2005, Allele quantification using molecular inversion probes (MIP), Nucleic Acids Research 33(21):e183.
Warner, 1996, A general method for the detection of large CAG repeat expansions by fluorescent PCR, J Med Genet 33(12):1022-6.
Warren, 2007, Assembling millions of short DNA sequences using SSAKE, Bioinformatics, 23:500-501.
Watson et al., 2004, Cystic fibrosis population carrier screening: 2004 revision of American College of Medical Genetics mutation panel, Genetics in Medicine 6(5):387-391.

(56) References Cited

OTHER PUBLICATIONS

Williams, 2003, Restriction endonucleases classification, properties, and applications, Mol Biotechnol 23(3):225-43.
Wittung, 1997, Extended DNA-Recognition Repertoire of Peptide Nucleic Acid (PNA): PNA-dsDNA Triplex Formed with Cytosine-Rich Homopyrimidine PNA, Biochemistry 36:7973.
Wu, 2001, Improved oligonucleotide sequencing by alkaline phosphatase and exonuclease digestions with mass spectrometry, Anal Biochem 290:347-352.
Wu, 1998, Sequencing regular and labeled oligonucleotides using enzymatic digestion and ionspray mass spectrometry, Anal Biochem 263:129-138.
Yau, 1996, Accurate diagnosis of carriers of deletions and duplications in Duchenne/Becker muscular dystrophy by fluorescent dosage analysis, J Med Gen 33(7):550-8.
Ye, 2009, Pindel: a pattern growth approach to detect break points of large deletions and medium size insertions from paired-end short reads, Bioinformatics 25(21):2865-2871.
Yoo, 2009, Applications of DNA microarray in disease diagnostics, J Microbiol Biotech19(7):635-46.
Yoon, 2014, MicroDuMIP: target-enrichment technique for microarray-based duplex molecular inversion probes, Nucl Ac Res 43(5):e28.
Yoshida, 2004, Role of BRCA1 and BRCA2 as regulators of DNA repair, transcription, and cell cycle in response to DNA damage. Cancer Science 95(11)866-71.
Yu, 2007, A novel set of DNA methylation markers in urine sediments for sensitive/specific detection of bladder cancer, Clin Cancer Res 13(24):7296-7304.
Yuan, 1981, Structure and mechanism of multifunctional restriction endonucleases, Ann Rev Biochem 50:285-319.
Zerbino, 2008, Velvet: Algorithms for de novo short read assembly using de Bruijn graphs, Genome Research 18(5):821-829.
Zhang, 2011, Is Mitochondrial tRNAphe Variant m.593T.Ca Synergistically Pathogenic Mutation in Chinese LHON Families with m.11778G.A? PLoS One 6(10):e26511.
Zhao, 2009, PGA4genomics for comparative genome assembly based on genetic algorithm optimization, Genomics 94(4):284-6.
Zheng, 2011, iAssembler: a package for de novo assembly of Roche-454/Sanger transcriptome sequences, BMC Bioinformatics 12:453.
Zhou, 2014, Bias from removing read duplication in ultra-deep sequencing experiments, Bioinformatics 30(8):1073-1080.
Zimmerman, 2010, A novel custom resequencing array for dilated cardiomyopathy, Gen Med 12(5):268-78.
Brinkman, 2004, Splice Variants as Cancer Biomarkers, Clin Biochem 37:584.
Cremers, 1998, Autosomal Recessive Retinitis Pigmentosa and Cone-Rod Dystrophy Caused by Splice Site Mutations in the Stargardt's Disease Gene ABCR, Hum Mol Gen 7(3):355.
Cronin, 1996, Cystic Fibrosis Mutation Detection by Hybridization to Light-Generated DNA Probe Arrays Human Mutation 7:244.
Kerem, 1989, Identification of the cystic fibrosis gene: genetic analysis, Science 245:1073-1080.
Schouten, 2002, Relative Quantification of 40 Nucleic Acid Sequences by Multiplex Ligation-Dependent Probe Amplification, Nucle Acids Res 30 (12):257.
Tkachuk, 1990, Detection of bcr-abl Fusion in Chronic Myelogeneous Leukemia by in Situ Hybridization, Science 250:559.
Tobler, 2005, The SNPlex Genotyping System: A Flexible and Scalable Platform for SNP Genotyping, J Biomol Tech 16(4):398.
Abravaya, 1995, Detection of point mutations with a modified ligase chain reaction (Gap-LCR), Nucleic Acids Research, 23(4): 675-682.
Adey, 2010, Rapid, low-input, low-bias construction of shotgun fragment libraries by high-density in vitro transposition, Genome Biol 11:R119.
Agrawal, 1990, Site-specific functionalization of oligodeoxynucleotides for non-radioactive labelling, Tetrahedron Let 31:1543-1546.
Akhras, 2007, PathogenMip Assay: a multiplex pathogen detection assay, PLoS One 2:e2230.
Archer, 2014, Selective and flexible depletion of problematic sequences from RNA-seq libraries at the cDNA stage, BMC Genomics 15(1):401.
Bhangale, 2006, Automating resequencing-based detection of insertion-deletion polymorphisms, Nature Genetics 38:1457-1462.
Brison, 1982, General method for cloning amplified DNA by differential screening, Mol Cell Biol 2(5):578-587.
Carpenter, 2013, Pulling out the 1%: whole-genome capture for the targeted enrichment of ancient DNA sequencing libraries, Am J Hum Genet 93(5):852-864.
Caruthers, 1985, Gene synthesis machines: DNA chemistry and its uses, Science 230:281-285.
Chen, 2010, Identification of racehorse and sample contamination by novel 24-plex STR system, Forensic Sci Int: Genetics 4:158-167.
Craig, 1997, Removal of repetitive sequences from FISH probes, Hum Genet 100:472.
Deorowicz, 2013, Data compression for sequencing data, Alg for Mole Bio 8:25.
Diep, 2012, Library-free methylation sequencing with bisulfite padlock probes, Nature Methods 9:270-272 (and supplemental information).
Dolinsek, 2013, Depletion of unwanted nucleic acid templates by selection cleavage: LNAzymes, catalytically active oligonucleotides containing locked nucleic acids, open a new window for detecting rare microbial community members, App Env Microbiol 79(5):1534-1544.
Drmanac, 1992, Sequencing by hybridization: towards an automated sequencing of one million M13 clones arrayed on membranes, Elctrophoresis 13:566-573.
Ericsson, 2008, A dual-tag microarray platform for high-performance nucleic acid and protein analyses, Nucl Acids Res 36:e45.
Flaschker, 2007, Description of the mutations in 15 subjects with variant forms of maple syrup urine disease, J Inherit Metab Dis 30:903-909.
Giusti, 1993, Synthesis and Characterization of f'-Fluorescent-dye-labeled Oligonucleotides, PCR Meth Appl 2:223-227.
Green, 2005, Suicide polymerase endonuclease restriction, a novel technique for enhancing PCR amplification of minor DNA template, Appl Env Microbiol 71(8):4721-4727.
Gupta, 1991, A general method for the synthesis of 3'-sulfhydryl and phosphate group containing oligonucleotides, Nucl Acids Res 19(11):3019-3025.
Gupta, 2014, Expanding the genetic toolkit: ZFNs, TALENs, and CRISPR-Cas9, J Clin Invest 124(10):4154.
Harris, 2008, Helicos True Single Molecule Sequencing (tSMS) Science 320:106-109.
Heger, 2006, Protonation of Cresol Red in Acidic Aqueous Solutions Caused by Freezing, J Phys Chem B 110(3):1277-1287.
Heid, 1996, Real time quantitative PCR, Genome Res 6:986-994.
Homer, 2008, Resolving Individuals Contributing Trace Amounts of DNA to Highly Complex Mixtures Using High-Density SNP Genotyping Microarrays. PLoS One 4(8):e1000167.
Housley, 2009, SNP discovery and haplotype analysis in the segmentally duplicated DRD5 coding region, Ann Hum Genet 73(3):274-282.
International Human Genome Sequencing Consortium, 2004, Finishing the euchromatic sequence of the human genome, Nature 431:931-945.
Isosomppi, 2009, Disease-causing mutations in the CLRN1 gene alter normal CLRN1 protien trafficking to the plasma membrane. Mol Vis 15:1806-1818.
Kambara, 1988, Optimization of Parameters in a DNA Sequenator Using Fluorescence Detection, Nature Biotechnology 6:816-821.
Kinde, 2012, FAST-SeqS: a simple an effective method for detection of aneuploidy by massively parallel sequencing, PLoS One 7(7):e41162.
Li, 2003, DNA binding and cleavage by the periplasmic nuclease Vvn: a novel structure with a known active site, Embo J 22(15):4014-4025.
Li, 2011, Improving SNP discovery by base alignment quality, Bioinformatics 27:1157.
Ma, 2006, Application of real-time polymerase chain reaction (RT-PCR), J Am Soc 1-15.

(56) References Cited

OTHER PUBLICATIONS

McDonnell, 2007, Antisepsis, disinfection, and sterilization: types, action, and resistance, p. 239.
Messiaen, 1999, Exon 10b of the NF1 gene represents a mutational hotspot and harbors a recurrent missense mutation Y489C associated with aberrant splicing, Genetics in Medicine, 1(6):248-253.
Meyer, 2007, Targeted high-throughput sequencing of tagged nucleic acid samples, Nucleic Acids Research 35(15):e97 (5 pages).
Miesenbock, 1998, Visualizing secretion and synaptic transmission with pH-sensitive green fluorescent proteins, Nature 394(6689):192-95.
Miller, 2010, Assembly algorithms for next-generation sequencing data, Genomics 95:315-327.
Miner, 2004, Molecular barcodes detect redundancy and contamination in hairpin-bisulfite PCR, Nucl Acids Res 32(17):e135.
Miyake, 2009, PIK3CA gene mutations and umplification in uterine cancers, Canc Lett 261:120-126.
Munne, 2012, Preimplantation genetic diagnosis for aneuploidy and translocations using array comparative genomic hybridization, Curr Genomics 13(6):463-470.
Nelson, 1989, Bifunctional oligonucleotide probes synthesized using a novel CPG support are able to detect single base pair mutations, Nucl Acids Res 17(18):7187-7194.
O'Roak, 2012, Multiplex targeted sequencing identifies recurrently mutated genes in autism spectrum disorders, Science 338(6114):1619-1622.
Okou, 2007, Microarray-based genomic selection for high-throughput reseuqencing, Nat Meth 4(11):907-909.
Parkinson, 2012, Preparation of high-quality next-generation sequencing libraries from picogram quantities of target DNA, Genome Res 22:125-133.
Pourmand, 2006, PathgoenMIPer: a tool for the design of molecular inversion probes, BMC informatics 7:500.
Qiagen, 2011, Gentra Puregene handbook, 3d Ed. (72 pages).
Saihan, 2009, Update on Usher syndrome, Curr Op Neurology 22(1):19-24.
Shagin, 2002, A novel method for SNP detection, Genome Res 12:1935.
Shen, 2011, High quality DNA sequence capture of 524 disease candidate genes, PNAS 108(16):6549-6554.
Smith, 1985, The synthesis of oligonucleotides containing an aliphatic amino group at the 5' terminus: synthesis of fluorescent DNA primers for use in DNA sequence analysis, Nucl Acid Res 13:2399-2412.
Smith, 2010, Highly-multiplexed barcode sequencing: an efficient method for parallel analysis of pooled samples, Nucleic Acids Research 38(13):e142 (8 pages).
Sproat, 1987, The synthesis of protected 5'-mercapto-2',5'-dideoxyribonucleoside-3'-O-phosphoramidites; uses of 5'-mercapto-oligodeoxyribonucleotides, Nucl Acid Res 15:4837-4848.
Streit, 2003, CTFR gene: molecular analysis in patients from South Brazil, Molecular Genetics and Metabolism 78:259-264.
Summerer, 2010, Targeted High Throughput Sequencing of a Cancer-Related Exome Subset by Specific Sequence Capture With a Fully Automated Microarray Platform, Genomics 95(4):241-246.
Tan, 2014, Clinical outcome of preimplantation genetic diagnosis and screening using next generation sequencing, GigaScience 3(30):1-9.
Treangen, 2011, Repetitive DNA and next-generation sequencing: computational challenges and solutions, Nat Rev Gen 13(1):36-46.

Wahl, 1979, Efficient transfer of large DNA fragments from agarose gels to diazobenzyloxymethyl-paper and rapid hybridization by using dextran sulfate, PNAS 76:3683-3687.
Waszak, 2010, Systematic inference of copy-number genotypes from personal genome sequencing data reveals extensive olfactory gene content diversity, PLoS Comp Biol 6(11):e1000988.
Wirth, 1999, Quantitative analysis of survival motor neuron copies, Am J Hum Genet 64:1340-1356.
Xu, 2012, FastUniq: A fast de novo duplicates removal tool for paired short reads, PLoS One 7(12):e52249.
Yershov, 1996, DNA analysis and diagnostics on oligonucleotide microchips, PNAS 93:4913-4918.
Zhulidov, 2004, Simple cDNA normalization using kamchatka crab duplex-specific nuclease, Nucl Acids Res 32(3):e37.
Zimran, 1990, A glucocerebrosidase fusion gene in Gaucher disease, J Clin Invest 85:219-222.
Zuckerman, 1987, Efficient methods for attachment of thiol specific probes to the 3'-ends of synthetic oligodeoxyribonucleotides, Nucl Acid Res 15(13):5305-5321.
Blasczyk, 1996, Sequence analysis of the 2nd intron revealed common sequence motifs providing the means for a unique sequencing based typing protocol of the HLA-A locus, Tissue Antigens, 47:102-110.
Chaisson, 2004, Fragment assembly with short reads, Bionormatics, 20:2067-2074.
Chou, 2010, DNA Sequence Capture and Enrichment by Microarray Followed by Next-Generation Sequencing for Targeted Resequencing: Neurofibromatosis Type 1 Gene as a Model, Clinical Chemistry, 56(1):62-72.
Daly, 2007, Multiplex Assay for Comprehensive Genotyping of Genes Involved in Drug Metabolism, Excretion, and Transport, Clinical Chemistry, 53:7:1222-1230.
Deng, 2012, Supplementary Material, Nature Biotechnology, S1-1-S1-1 1, Retrieved from the Internet on Oct. 24, 2012, 12 pages.
Dou, 2012, Reference-free SNP calling: improved accuracy by preventing incorrect calls from repetitive genomic regions, Biology Direct 7:17.
Fu, 2010, Repeat subtraction-mediated sequence capture from a complex genome, The Plant Journal, 62:898-909.
Jares, 2006, Genomic platforms for cancer research: potential diagonistic and prognastic applications in clinical oncology, Clin Transl Oncol, 8(3):161-72.
Johnson, 2005, Dark matter in the genome: evidence of widespread transcription detected by microarray tiling experiments. Trends in Genetics, 21(2):93-102.
Kotsch, 1999, Sequencing of HLA class II genes based on the conserved diversity of the non-coding regions: sequencing based typing of HLA-DRB genes, Tissue Antigens, 53:486-497.
Schiffman, 2007, Adapting molecular inversion probe (MIP) technology for allele quantification in childhood leukemia, Journal of Clinical Oncology, 25, p. 530, 5 pages.
Sonnhammer, 2002, Orthology, paralogy and proposed classification for paralog subtypes, Trends in Genetics, 18(12):619-620.
Tarhini, 2018, Predictive and on-treatment monitoring biomarkers in advanced melanoma: Moving toward personalized medicine. Cancer Treatment Reviews, 71:8-18.
Wang, 2007, Analysis of molecular inversion probe performance for allele copy number determination, Genome Biology, 8(11):R246.1-R246.14.

* cited by examiner

SCREENING FOR STRUCTURAL VARIANTS

CROSS-REFERENCE TO RELATED APPLICATION

This application is a continuation of U.S. patent application Ser. No. 14/989,073, filed Jan. 6, 2016, which claims priority to, and the benefit of, U.S. Provisional Patent Application No. 62/100,254, filed Jan. 6, 2015, the contents of each of which are incorporated by reference.

FIELD OF THE INVENTION

The invention relates to carrier screening and methods of detecting structural variant breakpoints using molecular inversion probes.

BACKGROUND

Molecular inversion probes (MIPs) can be used to capture targeted regions of a person's genetic material and to assay for disease-associated mutations. Each MIP has two linked oligonucleotide targeting arms that are designed to hybridize to a strand of nucleic acid in positions that flank a region of interest. In a typical assay, a set of MIPs is used to cover a gene segment of interest. Most of the MIPs hybridize to their intended target. Upon successful hybridization, the two targeting arms of one MIP are connected together in a ligation step into a covalently closed circle. Such assays are useful in interrogating the genome for mutations such as single-nucleotide polymorphisms.

Unfortunately, some mutations such as unexpected deletions, insertions, translocations, or inversions may be associated with an absent or incomplete targeting arm hybridization site and thus interfere with the ability of the MIPs to hybridize and be circularized. Unbound DNA and un-circularized MIPs are typically digested away by an exonuclease after which the circularized MIPs are used in amplification or sequencing reactions.

SUMMARY

Methods of the invention use MIPs to detect structural variants such as insertions, inversions, translocations, and deletions in a nucleic acid. Where a nucleic acid contains a structural variant, that nucleic acid may either lack one of the two hybridization sites for the two targeting arms of a MIP or one of the two arm targeting sites may be sufficiently separated such that the two arms of the probe will not connect as efficiently. Accordingly, that MIP effectively hybridizes to the genome with a single targeting arm. If a second MIP hybridizes in proximity to that first MIP, also by only one targeting arm, those two MIPs may be ligated together without being circularized. The second probe may hybridize by only one arm because the nucleic acid lacks one of its intended hybridization sites, or it could simply be the case this second arm has temporarily melted off the template molecule, thereby allowing the connection of the arm of probe 1 and probe. Since structural variants in the nucleic acid causes the two MIPs to be ligated together without circularization, detecting the two MIPs ligated together can reveal the presence of the insertion or deletion in the nucleic acid. If the un-circularized MIPs are discarded, as is common in MIP reactions, then information about structural variants gets thrown away. Instead, methods of the invention use the detection of un-circularized MIPs that have been ligated together to report the presence of an insertion, inversion, translocation, or deletion (structural variants) in the nucleic acid.

Reporting of structural variants via detection of MIPs ligated together may be performed as part of the same amplification and/or sequencing reactions that are also used to analyze the circularized MIPs. Thus, reporting of substitutions and structural variants through sequencing of circularized and non-circularized MIPs, respectively, may be provided in an assay that uses a single multiplex capture reaction.

Preferably, genomic DNA is captured using a set of MIPs designed to cover portions of genes of interest. Genomic DNA that is captured by the circularized MIPs can be sequenced to show substitutions or small structural variants in the genome while MIPs ligated together, or 'inter-probe products," are detected and used to describe a location of structural variants. While conventional MIP capture reactions digest the inter-probe product with exonuclease, methods of the invention may include protecting inter-probe product from exonuclease digestion, for example, by including a phosphorothioate base in the MIP backbone. Methods include detecting or sequencing the captured inter-probe product and reporting on a patient's genotype using information from sequencing both circularized probes and inter-probe product. Thus, methods of the invention provide genotyping assays that robustly and reliably detect and report mutations of different categories, such as small structural variants and substitutions as well as large chromosomal abnormalities. Methods of the invention have particular application in carrier screening, for reporting whether a patient is a carrier of a mutation that is associated with a Mendelian recessive genetic disease.

In certain aspects, the invention provides a method of identifying a mutation. The method includes exposing a nucleic acid to a plurality MIPs, each MIP having two targeting arms designed to hybridize upstream and downstream of a target in a genome. Two of the MIPs that each hybridizes to the nucleic acid by only one of their two targeting arms are connected together to create an inter-probe product. The method includes detecting the inter-probe product and detecting, identifying, or reporting a structural variant of the genome in the nucleic acid. The attaching may include filling in a gap between the two MIPs along the strand of nucleic acid using a polymerase, making a covalent attachment with a ligase, or both. Preferably, the method includes sequencing the inter-probe product to produce sequence reads, comparing the sequence reads to a reference genome, and describing a location of the structural variant within a gene associated with a Mendelian recessive hereditary disorder. A breakpoint in the nucleic acid based on the two MIPs that each hybridizes to the nucleic acid by a single targeting arm may be described. The structural variant may be identified as lying within an exon of a gene associated with the hereditary disorder. In some embodiments, the method includes producing a report that describes whether a person is a carrier of a hereditary disorder.

The method may include enzymatically converting at least some MIPs that hybridize to the nucleic acid by both targeting arms into covalently closed circles and sequencing at least a portion of the covalently closed MIPs to produce the sequence reads. Based on analysis of the sequence reads, one or more mutations in the nucleic acid from a person may be described in comparison to the reference genome. Methods of the invention may include multiplex sequencing and/or capture reactions. For example, MIPs may be exposed to the nucleic acid all free in solution and in one reaction volume. The method may include circularizing some of the MIPs (e.g., using ligase) and sequencing the circularized MIPs and the inter-probe product. The method may include digesting single-stranded nucleic acid material with an exonuclease prior to detecting the inter-probe product. In some embodiments, one or more MIPs include some moiety or feature to resist exonuclease digestion of that probe such as a phosphorothioate base or bases.

Aspects of the invention provide a method of identifying a structural variant that includes exposing a nucleic acid from a patient to a plurality of probes. Each probe has a linked pair of targeting arms designed to hybridize upstream and downstream of a target in a genome. Preferably, the plurality of probes is designed to cover at least a portion of a gene associated with a Mendelian recessive hereditary disorder. Two of the probes that hybridize to the nucleic acid are ligated together to create an inter-probe product, and some probes that hybridize to the nucleic acid by both targeting arms may be circularized. The method includes sequencing the inter-probe product and at least a portion of the circularized probes to produce sequence reads, which may be analyzed, e.g., by assembly or comparison to a reference genome. One or more substitution mutations and a structural variant within the gene are described as found in the nucleic acid from the patient.

In a preferred embodiment, the probes are molecular inversion probes that each include two linked targeting arms. For each probe, the arms include oligonucleotide portions that are designed to hybridize to portions of the nucleic acid that flank a target of interest. The hybridized probes are circularized, which may include extending one targeting arm with a polymerase and ligating the extended targeting arm to the other targeting arm to close the probe into a circle. Additionally, inter-probe products may be made by ligating pairs of probes together that are hybridized adjacent to one another along the nucleic acid. Making the inter-probe product may include filling in a gap between the two probes along the strand of nucleic acid using a polymerase and using a DNA ligase.

Methods may include a digestion step for the capture reaction. Single-stranded nucleic acid material may be digested with a nuclease prior to the sequencing. With the probes exposed to the nucleic acid, an exonuclease or a cocktail of exonucleases digests non-circularized product. Additionally, the probes may be designed to resist nuclease digestion when in inter-probe product form by, for example, inclusion of phosphorothioate base in the backbone.

The circularized probes and the inter-probe product may optionally be amplified and then preferably are sequenced to produce sequence reads. The sequence reads are assembled, compared to a reference, or both, to describe a genotype (e.g., of the patient from whom the nucleic acid was obtained). Where sequence reads vary from a reference, a mutation can be called and reported. For example, if a base of the person's DNA is different than the corresponding base in the reference, a substitution mutation may be reported. Where inter-probe product is present, a structural variant is reported. By using information about the target to which the pair of probes in the inter-probe product is designed to hybridize, a location of the structural variant in the patient's genome may be described. Thus methods of the invention may include producing a report that describes, within the patient's genome, both mutations such as substitutions or small indels as well as information on structural variants such as a location of a breakpoint. By these means, the methods may be used to produce a report that identifies that the patient is a carrier of the Mendelian recessive hereditary disorder.

In some aspects the invention provides a method of identifying splice forms (sometimes called isoforms). The method includes exposing a sample comprising cDNA or RNA to a plurality of molecular inversion probes (MIPs). Two of the MIPs via arms that have hybridized to the same cDNA or RNA molecule are connected together to create an inter-probe product, which is detected. The method includes identifying a splice form of an RNA transcript of a gene in the genome. The two MIPs may be connected together by filling in a gap between them along the cDNA molecular using a polymerase and using a ligase. Where the sample contains RNA, the polymerase may be a reverse transcriptase. The ligase could be, for example, a PBCV-1 DNA Ligase or *Chlorella* virus DNA Ligase, which catalyzes the ligation of adjacent, single-stranded DNA splinted by a complementary RNA strand. The method my further include sequencing the inter-probe product to produce sequence reads and analyzing the sequence reads to report one or more splice forms present in the sample.

DETAILED DESCRIPTION

The invention provides methods useful to identify large deletion variants in patient samples using a molecular inversion probe (MIP) assay that may be used in conjunction with sequencing such as next-generation short-read sequencing. Method of the invention provide for identification of otherwise difficult-to-characterize and often-deleterious variants. Assays that use MIP capture reactions and sequencing without employing methods of the invention may be found to be prone to false positive and false negative large deletion calls, thereby necessitating the use of extrinsic secondary tests. Methods of the invention are beneficial in addressing the high volume of output from next-generation sequencing (NGS) instruments. Particularly where NGS instruments have an extremely short read length, their ability to characterize indels larger than tens of bases is extremely limited. As many highly important deleterious variants are of large size (including CFTR del84, CFTR delExon2-3, HEXA del7.6 kb, NEB delExon55, and MCOLN del6.4 kb), NGS methods may not be adequate for genomic analysis of many important variants. Even where present MIP capture reactions are used to detect a specific deletion of interest, that deletion must be spanned by a single MIP. While efforts have been made to identify indels through depth of coverage, those efforts not only often require a known negative sample for comparison but also are susceptible to skewed read depth distributions due to uncontrollable changes in experimental conditions, making coverage comparisons challenging. The invention provides methods that avoid those limitations. Methods of the invention provide a complete carrier screening assay that can reliably report on variants in a patient's genome where the described and reported variants include both small variants such as mutations and short indels (e.g., between about 1 and tens of base pairs) as well as large deletions.

Figure 1:
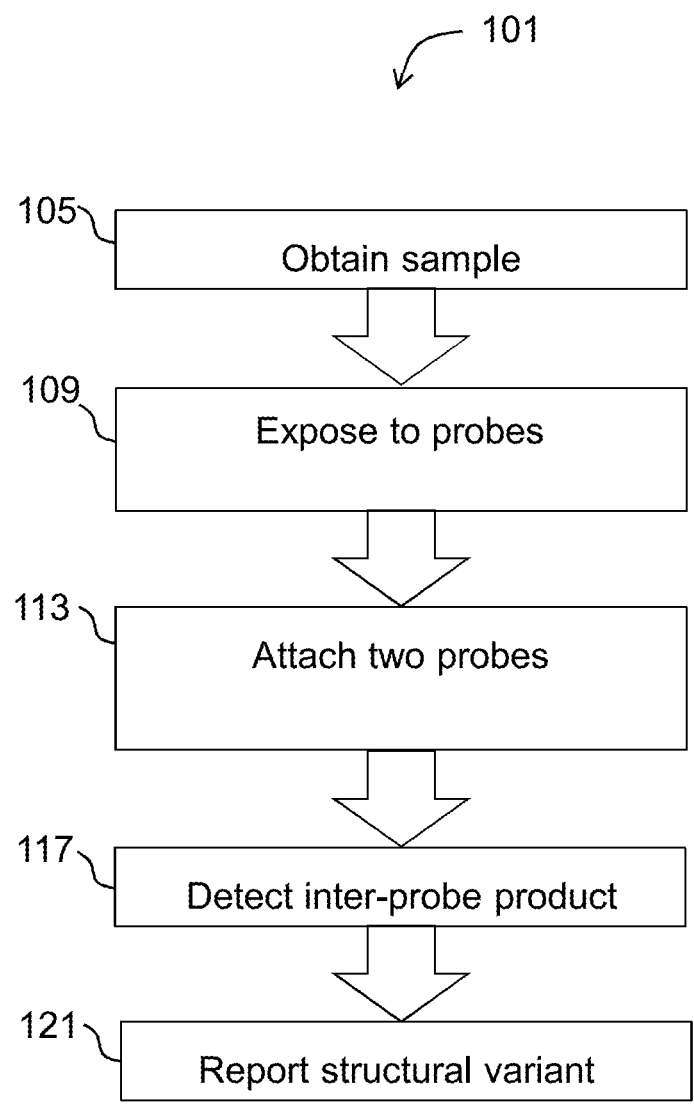
FIG. 1 diagrams a method for carrier screening that includes the ability to detect structural variant breakpoints using molecular inversion probes.

FIG. 1 diagrams a method 101 for to carrier screening that includes the ability to detect structural variant breakpoints using molecular inversion probes. In the depicted embodiment, the method includes obtaining 105 a nucleic acid sample from a person and exposing 109 the nucleic acid to a plurality of probes. Any suitable probe can be used where each probe provides a linked pair of targeting arms designed to hybridize upstream and downstream of a target in a genome. In a preferred embodiment, the probes are MIPs, e.g., as described in U.S. Pub. 2013/0274146, each incorporated by reference. Two of the probes are hybridized to the nucleic acid and attached 113 together to create an inter-probe product. After or as part of any optional amplification step, the inter-probe product is detected 117 and detection of the inter-probe product is used for reporting 121 a structural variant of the genome in the nucleic acid. An important benefit of the described method 101 is that the steps can be integrated within a MIP-based carrier screening assay where, for example, a plurality of MIPs are designed to tile along a target of interest, such as a portion of a gene known to harbor mutations associated with a genetic disorder. Such an assay can include sequencing the inter-probe product to produce sequence reads, which are then compared to a reference to describe a location of the structural variant within a gene associated with a Mendelian recessive hereditary disorder. Moreover, this may be done within an assay wherein at least some probes that hybridize to the nucleic acid by both targeting arms are enzymatically converted into covalently closed circles and some or all of the covalently closed probes are also sequenced. The resulting information produced by sequencing can be used to describe one or more mutations in the nucleic acid from the person in comparison to the reference genome. This provides an NGS-based platform for genetic carrier screening in a clinical setting. The MIPs can be designed and used to isolate a number of target regions of interest, for example, part or all of genes associated with known disorders, from genomic DNA by automated multiplex target capture. The isolated gDNA may be tagged with molecular barcodes, pooled, and sequenced, e.g., on an Illumina Hiseq system. Reads from each sample may be de-multiplexed, aligned to a reference, and integrated into accurate genotype calls which are then interrogated for pathogenic mutations. Using such methods, more than 40 k bp can be targeted by a set of MIPs designed to tile across the target such that each base is captured by at least three different probes.

For method 101, the sample that includes nucleic acid may be obtained 105 by any suitable method. The sample may be obtained from a tissue or body fluid that is obtained in any clinically acceptable manner. Body fluids may include mucous, blood, plasma, serum, serum derivatives, bile, blood, maternal blood, phlegm, saliva, sweat, amniotic fluid, menstrual fluid, mammary fluid, follicular fluid of the ovary, fallopian tube fluid, peritoneal fluid, urine, and cerebrospinal fluid (CSF), such as lumbar or ventricular CSF. A sample may also be a fine needle aspirate or biopsied tissue. A sample also may be media containing cells or biological material. Samples may also be obtained from the environment (e.g., air, agricultural, water and soil) or may include research samples (e.g., products of a nucleic acid amplification reaction, or purified genomic DNA, RNA, proteins, etc.).

Isolation, extraction or derivation of genomic nucleic acids may be performed by methods known in the art. Isolating nucleic acid from a biological sample generally includes treating a biological sample in such a manner that genomic nucleic acids present in the sample are extracted and made available for analysis. Generally, nucleic acids are extracted using techniques such as those described in Green & Sambrook, 2012, Molecular Cloning: A Laboratory Manual 4 edition, Cold Spring Harbor Laboratory Press, Cold Spring Harbor, N.Y. (2028 pages), the contents of which are incorporated by reference herein. A kit may be used to extract DNA from tissues and bodily fluids and certain such kits are commercially available from, for example, BD Biosciences Clontech (Palo Alto, Calif.), Epicentre Technologies (Madison, Wis.), Gentra Systems, Inc. (Minneapolis, Minn.), and Qiagen Inc. (Valencia, Calif.). User guides that describe protocols are usually included in such kits.

It may be preferable to lyse cells to isolate genomic nucleic acid. Cellular extracts can be subjected to other steps to drive nucleic acid isolation toward completion by, e.g., differential precipitation, column chromatography, extraction with organic solvents, filtration, centrifugation, others, or any combination thereof. The genomic nucleic acid may be resuspended in a solution or buffer such as water, Tris buffers, or other buffers. In certain embodiments the genomic nucleic acid can be re-suspended in Qiagen DNA hydration solution, or other Tris-based buffer of a pH of around 7.5.

Any nucleic acid may be analyzed using methods of the invention. Nucleic acids suitable for use in aspects of the invention may include without limit genomic DNA, genomic RNA, synthesized nucleic acids, whole or partial genome amplification product, and high molecular weight nucleic acids, e.g. individual chromosomes. In certain embodiments, a sample is obtained that includes double-stranded DNA, such as bulk genomic DNA from a subject, and the double-stranded DNA is then denatured. In some embodiments, a sample is obtained or prepared that includes cDNA and methods of the invention may be used to identify and quantify alternate splice forms or isoforms. As necessary or best-suited, double stranded nucleic acid may be denatured using any suitable method such as, for example, through the use of heat, detergent incubation, or an acidic or basic solution.

In some embodiments, it may be preferably to fragment the target nucleic acid for capture reactions. Without being bound by any mechanism, a set of probes may bind more successfully to target that has be fragmented. Nucleic acids, including genomic nucleic acids, can be fragmented using any of a variety of methods, such as mechanical fragmenting, chemical fragmenting, and enzymatic fragmenting. Methods of nucleic acid fragmentation are known in the art and include, but are not limited to, DNase digestion, sonication, mechanical shearing, and the like. U.S. Pub 2005/0112590 provides a general overview of various methods of fragmenting known in the art. Fragmentation of nucleic acid target is discussed in U.S. Pub. 2013/0274146.

Genomic nucleic acids can be fragmented into uniform fragments or randomly fragmented. In certain aspects, nucleic acids are fragmented to form fragments having a fragment length of about 5 kilobases or 100 kilobases. Desired fragment length and ranges of fragment lengths can be adjusted depending on the type of nucleic acid targets one seeks to capture and the design and type of probes such as molecular inversion probes (MIPs) that will be used. Chemical fragmentation of genomic nucleic acids can be achieved using methods such as a hydrolysis reaction or by altering temperature or pH. Nucleic acid may be fragmented by heating a nucleic acid immersed in a buffer system at a certain temperature for a certain period to time to initiate hydrolysis and thus fragment the nucleic acid. The pH of the buffer system, duration of heating, and temperature can be varied to achieve a desired fragmentation of the nucleic acid. Mechanical shearing of nucleic acids into fragments can be used e.g., by hydro-shearing, trituration through a needle, and sonication. The nucleic acid can also be sheared via nebulization, hydro-shearing, sonication, or others. See U.S. Pat. Nos. 6,719,449; 6,948,843; and 6,235,501. Nucleic acid may be fragmented enzymatically. Enzymatic fragmenting, also known as enzymatic cleavage, cuts nucleic acids into fragments using enzymes, such as endonucleases, exonucleases, ribozymes, and DNAzymes. Varying enzymatic fragmenting techniques are well-known in the art. Additionally, DNA may be denatured again as needed after the digestion and any other sample prep steps. For example, during a fragmentation step, ssDNA may anneal to form dsDNA and it may be desirable to again denature the dsDNA. In certain embodiments, the sample nucleic acid is captured or targeted using any suitable capture method or assay such as hybridization capture or capture by probes such as MIPs.

Figure 2:
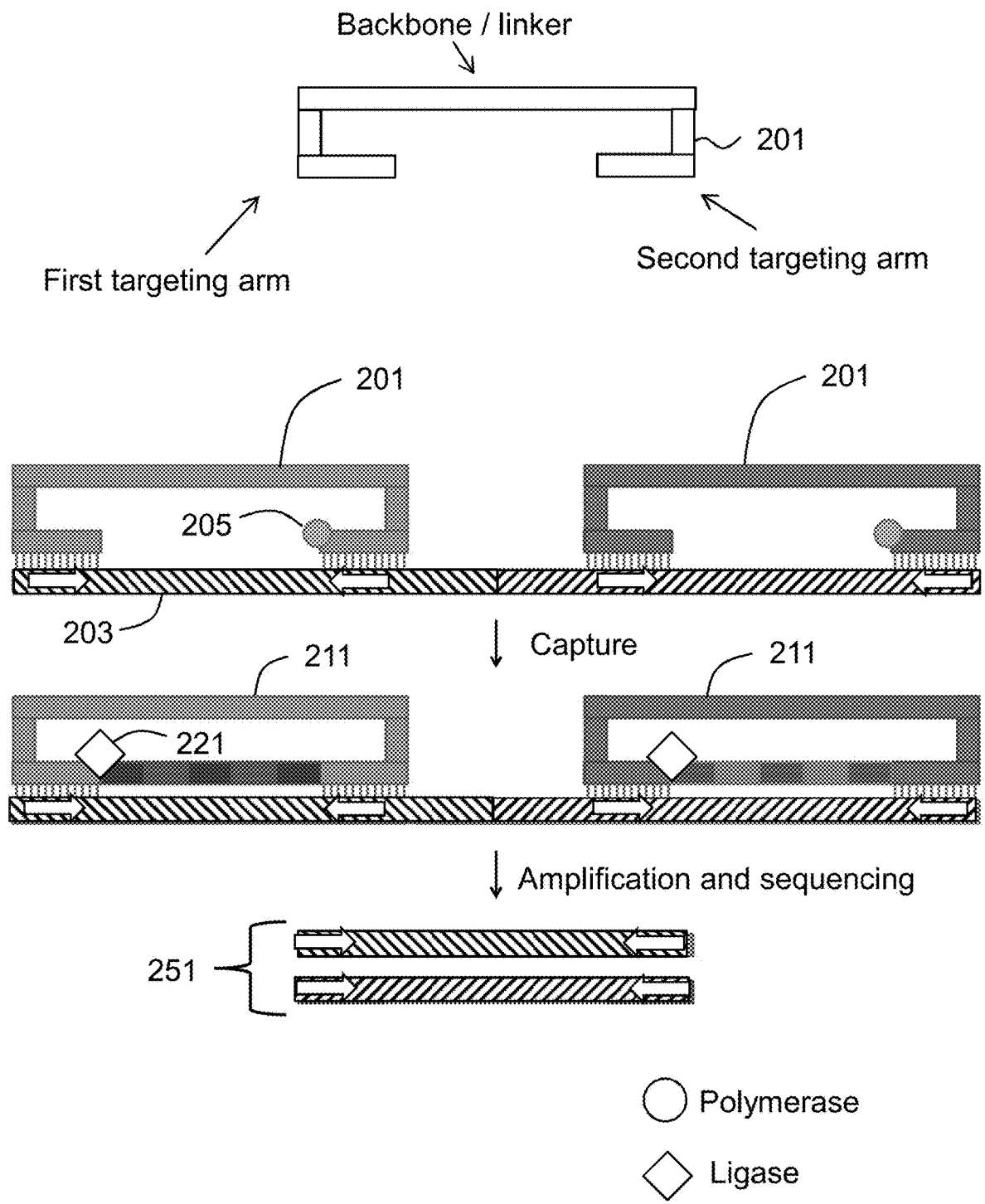
FIG. 2 illustrates use of MIPs to capture regions of target genomic material.

FIG. 2 illustrates use of MIPs 201 to capture regions of target genomic material 203 for amplification and sequencing. In order to provide for the accurate determination of large deletion variants using short-read sequencing, the invention provides an experimental and computational method to identify large deletion breakpoints using MIPs. Each MIP 201 contains a common backbone sequence and two complementary arms that are annealed to a DNA sample of interest. A polymerase 205 is utilized to fill in the gap between each of the two arms, and a ligase 221 is then utilized to create a set of circular molecules. Capture efficiency of the MIP to the target sequence on the nucleic acid fragment can be optimized by lengthening the hybridization and gap-filing incubation periods. (See, e.g., Turner et al., 2009, Massively parallel exon capture and library-free resequencing across 16 genomes, Nature Methods 6:315-316.) The resultant circular molecules 211 can be amplified using polymerase chain reaction to generate a targeted sequencing library. Here, the inventions provide methods wherein MIP capture reactions and sequencing/screening assays are extended to include the identification of arbitrarily large deletions and a variety of other classes of structural variations. These molecules can then be amplified using a common primer sequence present in the backbone, allowing a sequencing library to be generated from an arbitrary set of desired genomic target regions.

MIPs can be used to detect or amplify particular nucleic acid sequences in complex mixtures. Use of molecular inversion probes has been demonstrated for detection of single nucleotide polymorphisms (Hardenbol et al., 2005, Highly multiplexed molecular inversion probe genotyping: over 10,000 targeted SNPs genotyped in a single tube assay, Genome Res 15:269-75) and for preparative amplification of large sets of exons (Porreca et al., 2007, Multiplex amplification of large sets of human exons, Nat Methods 4:931-6 and Krishnakumar et al., 2008, A comprehensive assay for targeted multiplex amplification of human DNA sequences, PNAS 105:9296-301). One significant benefit of the method is in its capacity for a high degree of multiplexing, because generally thousands of targets may be captured in a single reaction containing thousands of probes. Thus the invention provides a multiplexed breakpoint detection and localization assay that may include identifying and reporting mutations or variants such as substitutions or small indels. The breakpoints detected in the multiplex assays may be associated with chromosomal rearrangements such as translocations, inversions, deletions, repetitions, wherein large segments (e.g., dozens or hundreds of base-pairs) of the genome are involved. Another significant benefit of the disclosed probe-based methods is that the methods may operate successfully with very small amounts of original target nucleic acid, unlike array-based methods, which require an abundance of target.

In some embodiments, the amount of target nucleic acid and probe used for each reaction is normalized to avoid any observed differences being caused by differences in concentrations or ratios. In some embodiments, in order to normalize genomic DNA and probe, the genomic DNA concentration is read using a standard spectrophotometer or by fluorescence (e.g., using a fluorescent intercalating dye). The probe concentration may be determined experimentally or using information specified by the probe manufacturer.

Once a locus has been captured, it may be amplified and/or sequenced in a reaction involving one or more primers. The amount of primer added for each reaction can range from 0.1 pmol to 1 nmol, 0.15 pmol to 1.5 nmol (for example around 1.5 pmol). However, other amounts (e.g., lower, higher, or intermediate amounts) may be used.

A targeting arm may be designed to hybridize (e.g., be complementary) to either strand of a genetic locus of interest if the nucleic acid being analyzed is DNA (e.g., genomic DNA). For MIP probes, whichever strand is selected for one targeting arm will be used for the other one. In the context of RNA analysis, a targeting arm should be designed to hybridize to the transcribed RNA. However, if cDNA is being targeted rather than RNA directly, the probes should be designed to be complementary to the reverse complement of the transcribed strand. It also should be appreciated that MIP probes referred to herein as "capturing" a target sequence are actually capturing it by template-based synthesis rather than by capturing the actual target molecule (other than for example in the initial stage when the arms hybridize to it or in the sense that the target molecule can remain bound to the extended MIP product until it is denatured or otherwise removed).

In certain embodiments, methods of the invention are used to identify a splice form. A sample that includes RNA or cDNA is exposed to a plurality of MIPs. Two of the MIPs are connected via arms that have hybridized to the same RNA or cDNA molecule to create an inter-probe product, which is detected and used to identify a splice form of an RNA transcript. The two MIPs may be connected using a polymerase and a ligase. Where the sample contains RNA, the polymerase may be a reverse transcriptase. The ligase could be, for example, a PBCV-1 DNA Ligase or *Chlorella* virus DNA Ligase, which catalyzes the ligation of adjacent, single-stranded DNA splinted by a complementary RNA strand. Once such ligase is the ligase sold under the trademark SPLINTR by New England BioLabs Inc. (Ipswich, Mass.).

A targeting arm may include a sequence that is complementary to one allele or mutation (e.g., a SNP or other polymorphism, a mutation, etc.) so that the probe will preferentially hybridize (and capture) target nucleic acids having that allele or mutation. Sequence tags (also referred to as barcodes) may be designed to be unique in that they do not appear at other positions within a probe or a family of probes and they also do not appear within the sequences being targeted. Uniformity and reproducibility can be increased by designing multiple probes per target, such that each base in the target is captured by more than one probe.

The length of a capture molecule on a nucleic acid fragment (e.g., a target nucleic acid or sub-region thereof) may be selected based upon multiple considerations. For example, where analysis of a target involves sequencing, e.g., with a next-generation sequencer, the target length should typically match the sequencing read-length so that shotgun library construction is not necessary. However, it should be appreciated that captured nucleic acids may be sequenced using any suitable sequencing technique as aspects of the invention are not limited in this respect.

Methods of the invention also provide for combining the method of fragmenting the nucleic acid prior to capture with other MIP capture techniques that are designed to increase target uniformity, reproducibility, and specificity. Other MIP capture techniques are shown in U.S. Pub. 2012/0165202, incorporated by reference.

Multiple probes, e.g., MIPs, can be used to amplify each target nucleic acid. In some embodiments, the set of probes for a given target can be designed to 'tile' across the target, capturing the target as a series of shorter sub targets. In some embodiments, where a set of probes for a given target is designed to 'tile' across the target, some probes in the set capture flanking non-target sequence. Alternately, the set can be designed to 'stagger' the exact positions of the hybridization regions flanking the target, capturing the full target (and in some cases capturing flanking non-target sequence) with multiple probes having different targeting arms, obviating the need for tiling. The particular approach chosen will depend on the nature of the target set. For example, if small regions are to be captured, a staggered-end approach might be appropriate, whereas if longer regions are desired, tiling might be chosen. In all cases, the amount of bias-tolerance for probes targeting pathological loci can be adjusted by changing the number of different MIPs used to capture a given molecule. Probes for MIP capture reactions may be synthesized on programmable microarrays to provide the large number of sequences required. See e.g., Porreca et al., 2007, Multiplex amplification of large sets of human exons, Nat Meth 4(11):931-936; Garber, 2008, Fixing the front end, Nat Biotech 26(10):1101-1104; Turner et al., 2009, Methods for genomic partitioning, Ann Rev Hum Gen 10:263-284; and Umbarger et al., 2014, Next-generation carrier screening, Gen Med 16(2):132-140. Using methods described herein, a single copy of a specific target nucleic acid may be amplified to a level that can be sequenced. Further, the amplified segments created by an amplification process such as PCR may be, themselves, efficient templates for subsequent PCR amplifications.

The result of MIP capture as described in FIG. 2 includes one or more circular target probes, which then can be processed in a variety of ways. Adaptors for sequencing may be attached during common linker-mediated PCR, resulting in a library with non-random, fixed starting points for sequencing. For preparation of a shotgun library, a common linker-mediated PCR is performed on the circle target probes, and the post-capture amplicons are linearly concatenated, sheared, and attached to adaptors for sequencing. Methods for shearing the linear concatenated captured targets can include any of the methods disclosed for fragmenting nucleic acids discussed above. In certain aspects, performing a hydrolysis reaction on the captured amplicons in the presence of heat is the desired method of shearing for library production. In addition to circularizing the MIPs for target capture, the invention includes the formation and detection of "cross-probe", or inter-probe, product.

Figure 3:
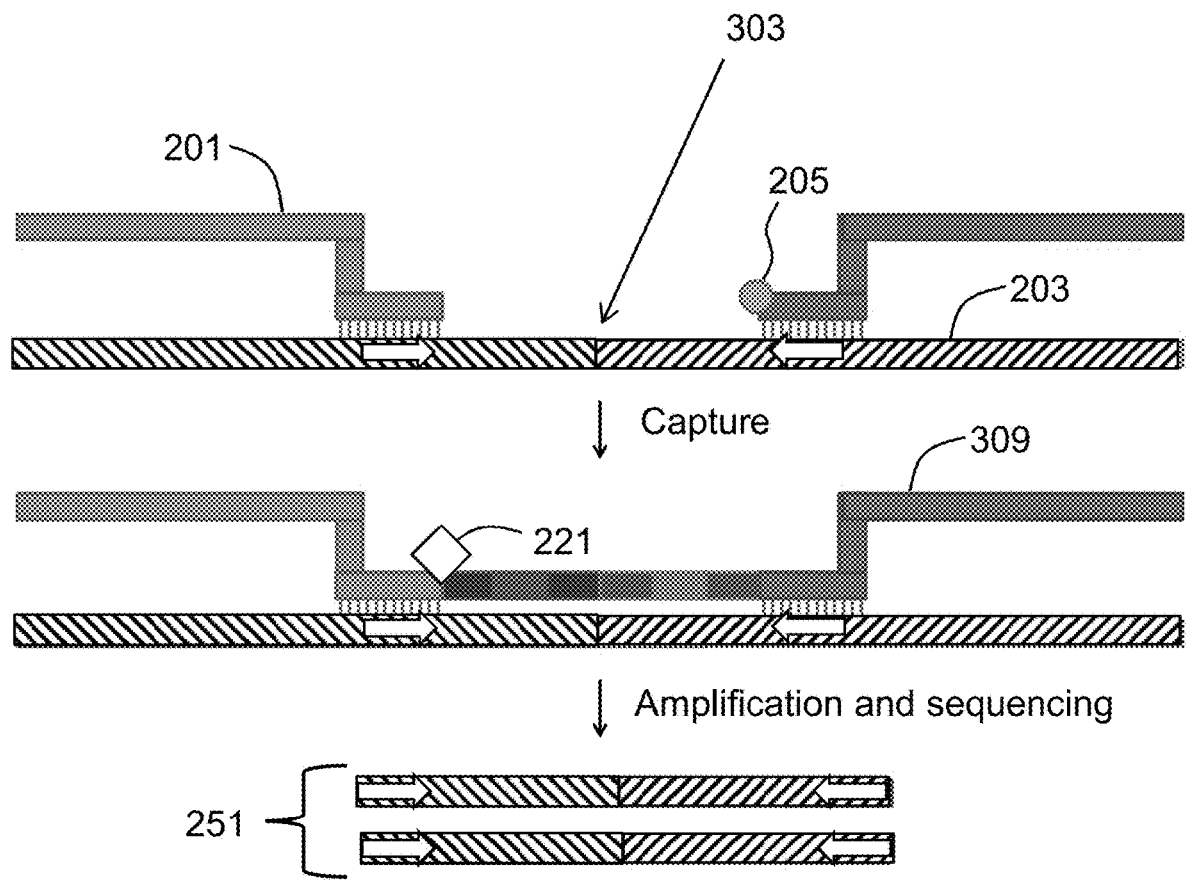
FIG. 3 illustrates the formation and detection of a "cross-probe", or inter-probe, product.

FIG. 3 illustrates the formation and detection of a "cross-probe", or inter-probe, product 309. While probes normally self-ligate into circular molecules, in the case of a large deletion or other classes of structural variants, one probe may hybridize to the target by only one probe arm. One probe arm from each of two probes spanning a deletion become ligated to each other. This ligation can include an extension, or "fill-in", step. This results in the formation of an inter-probe product 309 as shown in FIG. 3. Cross-probe products 309 may be amplified even when exonucleases are utilized to digest linear products. Inter-probe product 309 may be made resistant to exonuclease digestion via the inclusion of a phosphorothioate base or bases in the backbone of probes 201.

As described below, inter-probe product 309 may be sequenced along with circularized probe molecules. Additionally or alternatively, inter-probe product may be detected in parallel to or instead of sequencing to provide for detection of a deletion or other such chromosomal abnormality. Any suitable approach can be used to detect or describe deletion 303. In some embodiments, the detection of any inter-probe product 309 provides the inference that the patient's target DNA 203 includes the deletion 303 (that is, the very act of detection means that a breakpoint or deletion is included in a report). One approach to detection of deletions or breakpoints includes sequencing the inter-probe product 309. Methods may include attachment of amplification or sequencing adaptors or barcodes or a combination thereof to target DNA captured by probes.

Amplification or sequencing adapters or barcodes, or a combination thereof, may be attached to the fragmented nucleic acid. Such molecules may be commercially obtained, such as from Integrated DNA Technologies (Coralville, Iowa). In certain embodiments, such sequences are attached to the template nucleic acid molecule with an enzyme such as a ligase. Suitable ligases include T4 DNA ligase and T4 RNA ligase, available commercially from New England Biolabs (Ipswich, Mass.). The ligation may be blunt ended or via use of complementary overhanging ends. In certain embodiments, following fragmentation, the ends of the fragments may be repaired, trimmed (e.g. using an exonuclease), or filled (e.g., using a polymerase and dNTPs) to form blunt ends. In some embodiments, end repair is performed to generate blunt end 5' phosphorylated nucleic acid ends using commercial kits, such as those available from Epicentre Biotechnologies (Madison, Wis.). Upon generating blunt ends, the ends may be treated with a polymerase and dATP to form a template independent addition to the 3'-end and the 5'-end of the fragments, thus producing a single A overhanging. This single A can guide ligation of fragments with a single T overhanging from the 5'-end in a method referred to as T-A cloning. Alternatively, because the possible combination of overhangs left by the restriction enzymes are known after a restriction digestion, the ends may be left as-is, i.e., ragged ends. In certain embodiments double stranded oligonucleotides with complementary overhanging ends are used.

In certain embodiments, one or more barcodes is or are attached to each, any, or all of the fragments. A barcode sequence generally includes certain features that make the sequence useful in sequencing reactions. The barcode sequences are designed such that each sequence is correlated to a particular portion of nucleic acid, allowing sequence reads to be correlated back to the portion from which they came. Methods of designing sets of barcode sequences is shown for example in U.S. Pat. No. 6,235,475, the contents of which are incorporated by reference herein in their entirety. In certain embodiments, the barcode sequences range from about 5 nucleotides to about 15 nucleotides. In a particular embodiment, the barcode sequences range from about 4 nucleotides to about 7 nucleotides. In certain embodiments, the barcode sequences are attached to the template nucleic acid molecule, e.g., with an enzyme. The enzyme may be a ligase or a polymerase, as discussed above. Attaching bar code sequences to nucleic acid templates is shown in U.S. Pub. 2008/0081330 and U.S. Pub. 2011/0301042, the content of each of which is incorporated by reference herein in its entirety. Methods for designing sets of bar code sequences and other methods for attaching barcode sequences are shown in U.S. Pat. Nos. 7,537,897; 6,138,077; 6,352,828; 5,636,400; 6,172,214; and 5,863,722, the content of each of which is incorporated by reference herein in its entirety. After any processing steps (e.g., obtaining, isolating, fragmenting, amplification, or barcoding), nucleic acid can be sequenced.

Sequencing may be by any method known in the art. DNA sequencing techniques include classic dideoxy sequencing reactions (Sanger method) using labeled terminators or primers and gel separation in slab or capillary, sequencing by synthesis using reversibly terminated labeled nucleotides, pyrosequencing, 454 sequencing, Illumina/Solexa sequencing, allele specific hybridization to a library of labeled oligonucleotide probes, sequencing by synthesis using allele specific hybridization to a library of labeled clones that is followed by ligation, real time monitoring of the incorporation of labeled nucleotides during a polymerization step, polony sequencing, and SOLiD sequencing. Separated molecules may be sequenced by sequential or single extension reactions using polymerases or ligases as well as by single or sequential differential hybridizations with libraries of probes.

A sequencing technique that can be used includes, for example, Illumina sequencing. Illumina sequencing is based on the amplification of DNA on a solid surface using fold-back PCR and anchored primers. Genomic DNA is fragmented, and adapters are added to the 5' and 3' ends of the fragments. DNA fragments that are attached to the surface of flow cell channels are extended and bridge amplified. The fragments become double stranded, and the double stranded molecules are denatured. Multiple cycles of the solid-phase amplification followed by denaturation can create several million clusters of approximately 1,000 copies of single-stranded DNA molecules of the same template in each channel of the flow cell. Primers, DNA polymerase and four fluorophore-labeled, reversibly terminating nucleotides are used to perform sequential sequencing. After nucleotide incorporation, a laser is used to excite the fluorophores, and an image is captured and the identity of the first base is recorded. The 3' terminators and fluorophores from each incorporated base are removed and the incorporation, detection and identification steps are repeated. Sequencing according to this technology is described in U.S. Pat. Nos. 7,960,120; 7,835,871; 7,232,656; 7,598,035; 6,911,345; 6,833,246; 6,828,100; 6,306,597; 6,210,891; U.S. Pub. 2011/0009278; U.S. Pub. 2007/0114362; U.S. Pub. 2006/0292611; and U.S. Pub. 2006/0024681, each of which are incorporated by reference in their entirety.

Sequencing the inter-probe product 309 and the circularized MIPs produces a plurality of sequence reads. Reads generally include sequences of nucleotide data wherein read length may be associated with sequencing technology. For example, the single-molecule real-time (SMRT) sequencing technology of Pacific Bio produces reads thousands of base-pairs in length. For 454 pyrosequencing, read length may be about 700 bp in length. In some embodiments, reads are less than about 500 bases in length, or less than about 150 bases in length, or less than about 90 bases in length. In certain embodiments, reads are between about 80 and about 90 bases, e.g., about 85 bases in length. In some embodiments, these are very short reads, i.e., less than about 50 or about 30 bases in length. Sequence reads 251 can be analyzed to detect and describe the deletion 303 in target nucleic acid 203.

Figure 4:
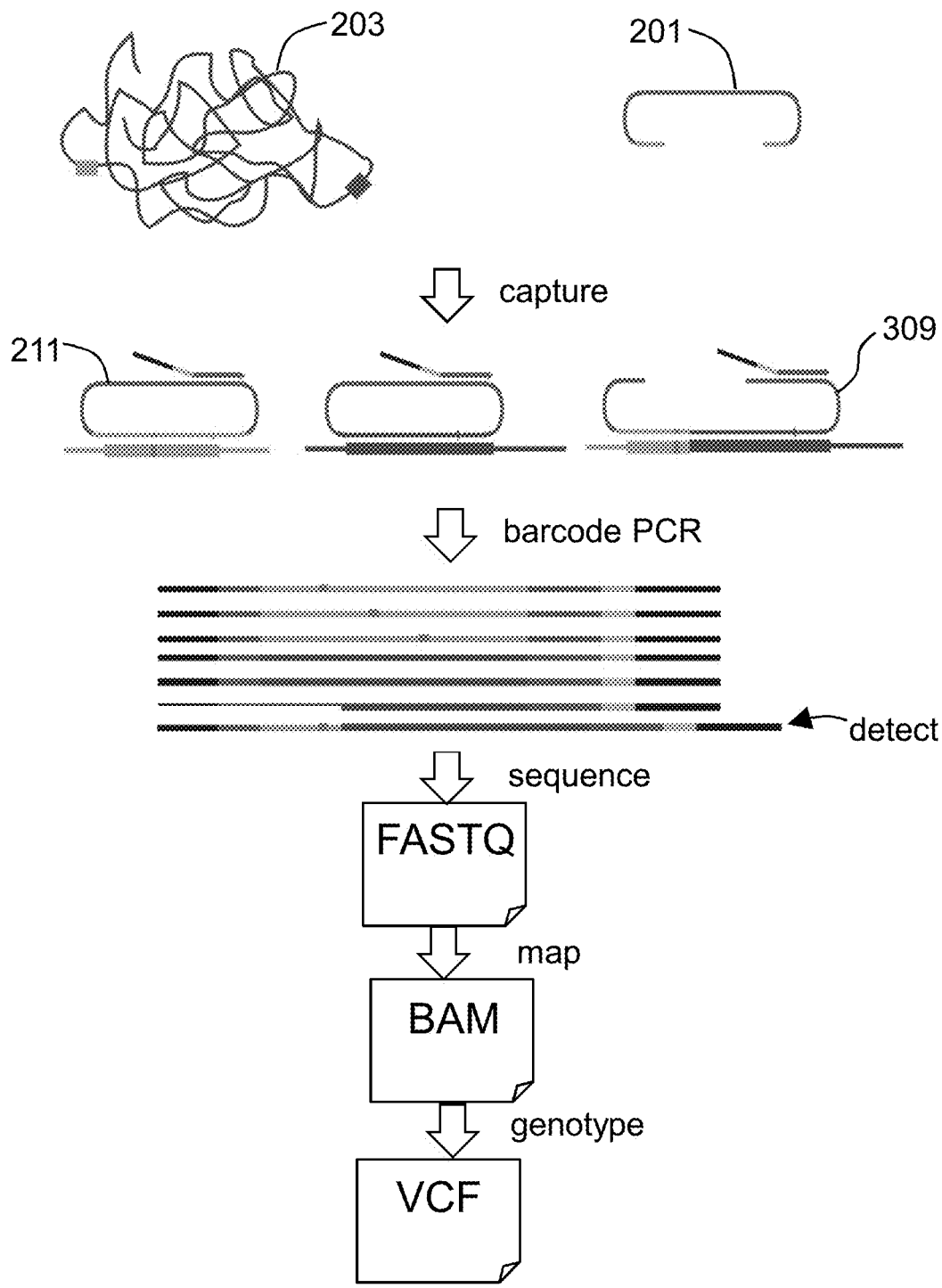
FIG. 4 gives a diagram of a workflow for deletion detection.

FIG. 4 gives a diagram of a workflow for deletion detection. Genomic DNA 203 is used as a starting sample and is exposed to a plurality of MIPs 201. Hybridization of the MIPs provides circularized probe product 211 and inter-probe product 309. Inter-probe product 309 is detected, which may include amplification, sequencing, micro-array detection, size fractionation, gel electrophoresis, other methods, or combinations thereof. In some embodiments, micro-arrays are used to detect inter-probe product. In certain embodiments, amplification and/or sequencing are used. Barcode PCR may be performed to provide amplicon material for sequencing and to attach sample-specific molecular barcodes. The amplicons and barcodes may then be sequenced and inter-probe product 309 detected. Sequencing produces a plurality of sequence reads that may be analyzed for breakpoint detection.

Sequence read data can be stored in any suitable file format including, for example, VCF files, FASTA files or FASTQ files, as are known to those of skill in the art. In some embodiments, PCR product is pooled and sequenced (e.g., on an Illumina HiSeq 2000). Raw .bcl files are converted to qseq files using bclConverter (Illumina). FASTQ files are generated by "de-barcoding" genomic reads using the associated barcode reads; reads for which barcodes yield no exact match to an expected barcode, or contain one or more low-quality base calls, may be discarded. Reads may be stored in any suitable format such as, for example, FASTA or FASTQ format.

FASTA is originally a computer program for searching sequence databases and the name FASTA has come to also refer to a standard file format. See Pearson & Lipman, 1988, Improved tools for biological sequence comparison, PNAS 85:2444-2448. A sequence in FASTA format begins with a single-line description, followed by lines of sequence data. The description line is distinguished from the sequence data by a greater-than (">") symbol in the first column. The word following the ">" symbol is the identifier of the sequence, and the rest of the line is the description (both are optional). There should be no space between the ">" and the first letter of the identifier. It is recommended that all lines of text be shorter than 80 characters. The sequence ends if another line starting with a ">" appears; this indicates the start of another sequence.

The FASTQ format is a text-based format for storing both a biological sequence (usually nucleotide sequence) and its corresponding quality scores. It is similar to the FASTA format but with quality scores following the sequence data. Both the sequence letter and quality score are encoded with a single ASCII character for brevity. The FASTQ format is a de facto standard for storing the output of high throughput sequencing instruments such as the Illumina Genome Analyzer. Cock et al., 2009, The Sanger FASTQ file format for sequences with quality scores, and the Solexa/Illumina FASTQ variants, Nucleic Acids Res 38(6):1767-1771.

For FASTA and FASTQ files, meta information includes the description line and not the lines of sequence data. In some embodiments, for FASTQ files, the meta information includes the quality scores. For FASTA and FASTQ files, the sequence data begins after the description line and is present typically using some subset of IUPAC ambiguity codes optionally with "-". In a preferred embodiment, the sequence data will use the A, T, C, G, and N characters, optionally including "-" or U as-needed (e.g., to represent gaps or uracil, respectively).

Following sequencing, reads may be mapped to a reference using assembly and alignment techniques known in the art or developed for use in the workflow. Various strategies for the alignment and assembly of sequence reads, including the assembly of sequence reads into contigs, are described in detail in U.S. Pat. No. 8,209,130, incorporated herein by reference. Strategies may include (i) assembling reads into contigs and aligning the contigs to a reference; (ii) aligning individual reads to the reference; (iii) assembling reads into contigs, aligning the contigs to a reference, and aligning the individual reads to the contigs; or (iv) other strategies known to be developed or known in the art. Sequence assembly can be done by methods known in the art including reference-based assemblies, de novo assemblies, assembly by alignment, or combination methods. Sequence assembly is described in U.S. Pat. No. 8,165,821; 7,809,509; 6,223,128; U.S. Pub. 2011/0257889; and U.S. Pub. 2009/0318310, the contents of each of which are hereby incorporated by reference in their entirety. Sequence assembly or mapping may employ assembly steps, alignment steps, or both. Assembly can be implemented, for example, by the program 'The Short Sequence Assembly by k-mer search and 3' read Extension '(SSAKE), from Canada's Michael Smith Genome Sciences Centre (Vancouver, B.C., CA) (see, e.g., Warren et al., 2007, Assembling millions of short DNA sequences using SSAKE, Bioinformatics, 23:500-501). SSAKE cycles through a table of reads and searches a prefix tree for the longest possible overlap between any two sequences. SSAKE clusters reads into contigs.

Greater detail on sequence assembly or interpretation and variant calling is given below. Methods of the invention may be used to describe mutations both of a large structural type (e.g., large deletions or structural variants, chromosomal abnormalities, breakpoints) and of a small localized type (e.g., substitutions, small indels).

Any suitable approach can be used to detect or describe deletion or other structural variants 303 or splice forms or isoforms. In some embodiments, the detection of any inter-probe product 309 provides the inference that the patient's target DNA 201 includes the structural variant 303. In certain embodiments, analysis of the sequence reads (e.g., from the circularized MIPs) includes analysis designed to report the presence or location of the structural variant 303. One approach to reporting the presence or location of structural variant 303 is to identify any targeted regions from which an abundance of sequence reads from inter-probe product 309 are produced. Such reads can be detected by targeting arms from either end that are not from the same MIP (i.e., a circularized MIP may provide sequence reads with certain expected barcode ends). Where inter-probe product reads appear, a software program may be used to search for a candidate large deletion by attempting to identify a specific novel breakpoint in those "cross-probe" reads. This approach allows any known or novel large deletions to be identified as long as one or more MIPs cover the breakpoints.

By utilizing a software program to search for an enrichment or the presence of cross-probe products and then examining the individual reads to locate a breakpoint, known or novel large deletions can be identified even in a short-read sequencing experiment.

In certain embodiments, analysis of the sequence reads (e.g., from the circularized MIPs) includes analysis designed to report the presence or location of deletion 303. One approach to reporting the presence or location of deletion 303 is to identify any targeted regions from which an abundance of sequence reads from inter-probe product 309 are produced. Such reads can be detected by targeting arm sequence from either end that are not from the same MIP (i.e., a circularized MIP may provide sequence reads with certain expected barcode ends). Where inter-probe product reads appear, a software program may be used to search for a candidate large deletion by attempting to identify a specific novel breakpoint in those "cross-probe" reads. This approach allows any known or novel large deletions to be identified as long as one or more MIPs cover the breakpoints.

In some embodiments, large genomic structural variants are detected through the assembly and analysis of the sequence reads, which process may also be used to detect and describe small localized variants. Generally, read assembly and analysis will proceed through the use of one or more specialized computer programs.

One read assembly program is Forge Genome Assembler, written by Darren Platt and Dirk Evers and available through the SourceForge web site maintained by Geeknet (Fairfax, Va.) (see, e.g., DiGuistini et al., 2009, De novo sequence assembly of a filamentous fungus using Sanger, 454 and Illumina sequence data, Genome Biology, 10:R94). Forge distributes its computational and memory consumption to multiple nodes, if available, and has therefore the potential to assemble large sets of reads. Forge was written in C++ using the parallel MPI library. Forge can handle mixtures of reads, e.g., Sanger, 454, and Illumina reads.

Another exemplary read assembly program known in the art is Velvet, available through the web site of the European Bioinformatics Institute (Hinxton, UK) (Zerbino & Birney, Velvet: Algorithms for de novo short read assembly using de Bruijn graphs, Genome Research 18(5):821-829). Velvet implements an approach based on de Bruijn graphs, uses information from read pairs, and implements various error correction steps.

Read assembly can be performed with the programs from the package SOAP, available through the website of Beijing Genomics Institute (Beijing, CN) or BGI Americas Corporation (Cambridge, Mass.). For example, the SOAPdenovo program implements a de Bruijn graph approach. SOAP3/GPU aligns short reads to a reference sequence.

Another read assembly program is ABySS, from Canada's Michael Smith Genome Sciences Centre (Vancouver, B.C., CA) (Simpson et al., 2009, ABySS: A parallel assembler for short read sequence data, Genome Res., 19(6):1117-23). ABySS uses the de Bruijn graph approach and runs in a parallel environment.

Read assembly can also be done by Roche's GS De Novo Assembler, known as gsAssembler or Newbler (NEW assemBLER), which is designed to assemble reads from the Roche 454 sequencer (described, e.g., in Kumar & Blaxter, 2010, Comparing de novo assemblers for 454 transcriptome data, Genomics 11:571 and Margulies 2005). Newbler accepts 454 Flx Standard reads and 454 Titanium reads as well as single and paired-end reads and optionally Sanger reads. Newbler is run on Linux, in either 32 bit or 64 bit versions. Newbler can be accessed via a command-line or a Java-based GUI interface. Additional discussion of read assembly may be found in Li et al., 2009, The Sequence alignment/map (SAM) format and SAMtools, Bioinformatics 25:2078; Lin et al., 2008, ZOOM! Zillions Of Oligos Mapped, Bioinformatics 24:2431; Li & Durbin, 2009, Fast and accurate short read alignment with Burrows-Wheeler Transform, Bioinformatics 25:1754; and Li, 2011, Improving SNP discovery by base alignment quality, Bioinformatics 27:1157. Assembled sequence reads may preferably be aligned to a reference. Methods for alignment and known in the art and may make use of a computer program that performs alignment, such as Burrows-Wheeler Aligner.

Aligned or assembled sequence reads may be analyzed for the detection of deletion 303. For example, where inter-probe product 309 is present, the sequence reads that result from that inter-probe product may be aligned to a reference with a liberal allowance for a deletion. In fact, known alignment methods (e.g., Smith-Waterman) can be adjusted to prefer one large deletion for such a set of reads. Breakpoint detection may include methodologies discussed in Ye et al., 2009, Pindel: a pattern growth approach to detect break points of large deletions and medium size insertions from paired-end short reads, Bioinformatics 25(21):2865-2871. For additional background, see Furtado et al., 2011, Characterization of large genomic deletions in the FBN1 gene using multiplex ligation-dependent probe amplification, BMC Med Gen 12:119-125; Nuttle et al., 2014, Resolving genomic disorder-associated breakpoints within segmental DNA duplications using massively parallel sequencing, Nat Prot 9(6):1496-1513; and Okeniewski et al., 2013, Precise breakpoint localization of large genomic deletions using PacBio and Illumina next-generation sequencers, Biotechniques 54(2):98-100. the contents of each of which are incorporated by reference.

Besides just detecting large deletions, methods of the invention can be used to detect and describe other types of mutations. Mutation calling is described in U.S. Pub. 2013/0268474. In certain embodiments, analyzing the reads includes assembling the sequence reads and then genotyping the assembled reads.

In certain embodiments, reads are aligned to hg18 on a per-sample basis using Burrows-Wheeler Aligner version 0.5.7 for short alignments, and genotype calls are made using Genome Analysis Toolkit. See McKenna et al., 2010, The Genome Analysis Toolkit: a MapReduce framework for analyzing next-generation DNA sequencing data, Genome Res 20(9):1297-1303 (aka the GATK program). High-confidence genotype calls may be defined as having depth≥50 and strand bias score≤0. De-barcoded fastq files are obtained as described above and partitioned by capture region (exon) using the target arm sequence as a unique key. Reads are assembled in parallel by exon using SSAKE version 3.7 with parameters "–m 30 –o 15". The resulting contiguous sequences (contigs) can be aligned to hg18 (e.g., using BWA version 0.5.7 for long alignments with parameter "–r 1"). In some embodiments, short-read alignment is performed as described above, except that sample contigs (rather than hg18) are used as the input reference sequence. Software may be developed in Java to accurately transfer coordinate and variant data (gaps) from local sample space to global reference space for every BAM-formatted alignment. Genotyping and base-quality recalibration may be performed on the coordinate-translated BAM files using the GATK program.

In some embodiments, any or all of the steps of the invention are automated. For example, a Perl script or shell script can be written to invoke any of the various programs discussed above (see, e.g., Tisdall, Mastering Perl for Bioinformatics, O'Reilly & Associates, Inc., Sebastopol, Calif. 2003; Michael, R., Mastering Unix Shell Scripting, Wiley Publishing, Inc., Indianapolis, Ind. 2003). Alternatively, methods of the invention may be embodied wholly or partially in one or more dedicated programs, for example, each optionally written in a compiled language such as C++ then compiled and distributed as a binary. Methods of the invention may be implemented wholly or in part as modules within, or by invoking functionality within, existing sequence analysis platforms. In certain embodiments, methods of the invention include a number of steps that are all invoked automatically responsive to a single starting queue (e.g., one or a combination of triggering events sourced from human activity, another computer program, or a machine). Thus, the invention provides methods in which any or the steps or any combination of the steps can occur automatically responsive to a queue. Automatically generally means without intervening human input, influence, or interaction (i.e., responsive only to original or pre-queue human activity).

Mapping sequence reads to a reference, by whatever strategy, may produce output such as a text file or an XML file containing sequence data such as a sequence of the nucleic acid aligned to a sequence of the reference genome. In certain embodiments mapping reads to a reference produces results stored in SAM or BAM file (e.g., as shown in FIG. 4) and such results may contain coordinates or a string describing one or more mutations in the subject nucleic acid relative to the reference genome. Alignment strings known in the art include Simple UnGapped Alignment Report (SUGAR), Verbose Useful Labeled Gapped Alignment Report (VULGAR), and Compact Idiosyncratic Gapped Alignment Report (CIGAR). See Ning et al., 2001, SSAHA: A fast search method for large DNA database, Genome Research 11(10):1725-9. These strings are implemented, for example, in the Exonerate sequence alignment software from the European Bioinformatics Institute (Hinxton, UK).

In some embodiments, a sequence alignment is produced—such as, for example, a sequence alignment map (SAM) or binary alignment map (BAM) file—comprising a CIGAR string (the SAM format is described, e.g., in Li, et al., The Sequence Alignment/Map format and SAMtools, Bioinformatics, 2009, 25(16):2078-9). In some embodiments, CIGAR displays or includes gapped alignments one-per-line. CIGAR is a compressed pairwise alignment format reported as a CIGAR string. A CIGAR string is useful for representing long (e.g. genomic) pairwise alignments. A CIGAR string is used in SAM format to represent alignments of reads to a reference genome sequence.

A CIGAR string follows an established motif. Each character is preceded by a number, giving the base counts of the event. Characters used can include M, I, D, N, and S (M=match; I=insertion; D=deletion; N=gap; S=substitution). The CIGAR string defines the sequence of matches/mismatches and deletions (or gaps). For example, the CIGAR string 2MD3M2D2M will mean that the alignment contains 2 matches, 1 deletion (number 1 is omitted in order to save space), 3 matches, 2 deletions and 2 matches. In general, for carrier screening or other assays such as the NGS workflow depicted in FIG. 5, sequencing results will be used in genotyping.

Output from mapping may be stored in a SAM or BAM file, in a variant call format (VCF) file, or other format. In an illustrative embodiment, output is stored in a VCF file. A typical VCF file will include a header section and a data section. The header contains an arbitrary number of meta-information lines, each starting with characters '##', and a TAB delimited field definition line starting with a single '#' character. The field definition line names eight mandatory columns and the body section contains lines of data populating the columns defined by the field definition line. The VCF format is described in Danecek et al., 2011, The variant call format and VCFtools, Bioinformatics 27(15):2156-2158.

The data contained in a VCF file represents the variants, or mutations, that are found in the nucleic acid that was obtained from the sample from the patient and sequenced. In its original sense, mutation refers to a change in genetic information and has come to refer to the present genotype that results from a mutation. As is known in the art, mutations include different types of mutations such as substitutions, insertions or deletions (INDELs), translocations, inversions, chromosomal abnormalities, and others. By convention in some contexts where two or more versions of genetic information or alleles are known, the one thought to have the predominant frequency in the population is denoted the wild type and the other(s) are referred to as mutation(s). In general in some contexts an absolute allele frequency is not determined (i.e., not every human on the planet is genotyped) but allele frequency refers to a calculated probable allele frequency based on sampling and known statistical methods and often an allele frequency is reported in terms of a certain population such as humans of a certain ethnicity. Variant can be taken to be roughly synonymous to mutation but referring to a genotype being described in comparison or with reference to a reference genotype or genome. For example as used in bioinformatics variant describes a genotype feature in comparison to a reference such as the human genome (e.g., hg18 or hg19 which may be taken as a wild type). Methods described herein generate data representing a location of a breakpoint or deletion in the genome of a patient, which data may further also represent one or more mutations, or "variant calls."

A description of a mutation may be provided according to a systematic nomenclature. For example, a variant can be described by a systematic comparison to a specified reference which is assumed to be unchanging and identified by a unique label such as a name or accession number. For a given gene, coding region, or open reading frame, the A of the ATG start codon is denoted nucleotide +1 and the nucleotide 5' to +1 is −1 (there is no zero). A lowercase g, c, or m prefix, set off by a period, indicates genomic DNA, cDNA, or mitochondrial DNA, respectively.

A systematic name can be used to describe a number of variant types including, for example, substitutions, deletions, insertions, and variable copy numbers. A substitution name starts with a number followed by a "from to" markup. Thus, 199A>G shows that at position 199 of the reference sequence, A is replaced by a G. A deletion is shown by "del" after the number. Thus 223delT shows the deletion of T at nt 223 and 997-999del shows the deletion of three nucleotides (alternatively, this mutation can be denoted as 997-999delTTC). In short tandem repeats, the 3' nt is arbitrarily assigned; e.g. a TG deletion is designated 1997-1998delTG or 1997-1998del (where 1997 is the first T before C). Insertions are shown by ins after an interval. Thus 200-201insT denotes that T was inserted between nts 200 and 201. Variable short repeats appear as 997(GT)N-N'. Here, 997 is the first nucleotide of the dinucleotide GT, which is repeated N to N' times in the population.

Variants in introns can use the intron number with a positive number indicating a distance from the G of the invariant donor GU or a negative number indicating a distance from an invariant G of the acceptor site AG. Thus, IVS3+1C>T shows a C to T substitution at nt +1 of intron 3. In any case, cDNA nucleotide numbering may be used to show the location of the mutation, for example, in an intron. Thus, c.1999+1C>T denotes the C to T substitution at nt +1 after nucleotide 1997 of the cDNA. Similarly, c.1997-2A>C shows the A to C substitution at nt −2 upstream of nucleotide 1997 of the cDNA. When the full length genomic sequence is known, the mutation can also be designated by the nt number of the reference sequence.

Relative to a reference, a patient's genome may vary by more than one mutation, or by a complex mutation that is describable by more than one character string or systematic name. The invention further provides systems and methods for describing more than one variant using a systematic name. For example, two mutations in the same allele can be listed within brackets as follows: [1997G>T; 2001A>C]. Systematic nomenclature is discussed in den Dunnen & Antonarakis, 2003, Mutation Nomenclature, Curr Prot Hum Genet 7.13.1-7.13.8 as well as in Antonarakis and the Nomenclature Working Group, 1998, Recommendations for a nomenclature system for human gene mutations, Human Mutation 11:1-3. By such means, a mutation can be described in the property index file of a variant node.

Any suitable gene may be screened using methods of the invention. In a preferred embodiments, methods of the invention are used to screen for recessive Mendelian disorders. Certain genetic disorders and their associated genes that may be screened using methods of the invention include Canavan disease (ASPA), cystic fibrosis (CFTR), glycogen storage disorder type 1a (G6PC), Niemann-Pick disease (SMPD1), Tay-Sachs disease (HEXA), Bloom syndrome (BLM), Fanconi anemia C (FANCC), familial Hyperinsulinism (ABCC8), maple syrup urine disease type 1A (BCKDHA) and type 1B (BCKDHB), Usher syndrome type III (CLRN1), dihydrolipoamide dehydrogenase deficiency (DLD), familial dysautonomia (IKBKAP), mucolipidosis type IV (MCOLN1), and Usher syndrome type 1F (PCDH15).

Methods of the invention may include detecting and describing genotype features such as mutations in a patient's genome and using a database for look-up, comparisons, or storage. In some embodiments, where a novel mutation is detected, it is classified and if pathogenic according to classification criteria, then it is entered into a database for use in future assays and comparisons. For one suitable database architecture, see U.S. Pat. No. 8,812,422, incorporated by reference. Using methods of the invention, single nucleotide substitutions or insertions/deletions not exceeding 10 bp (e.g., that are located in exons or within the first 10 bp of an intron) as well as gross chromosomal rearrangements, such as deletions, translocations, and inversions may be detected or stored. Variants may be named according to HGVS-recommended nomenclature or any other systematic mutation nomenclature. Mutations in the database (e.g., for comparison to sequencing results from a MIP carrier screening) may be classified. Classification criteria described here apply to recessive Mendelian disorders and highly penetrant variants with relatively large effects. Classification criteria may follow recommendations in the literature: Richards et al., ACMG recommendations for standards for interpretation and reporting of sequence variations: Revisions 2007, Genet Med 2008, 10:294-300; Maddalena et al., Technical standards and guidelines: molecular genetic testing for ultra-rare disorders, Genet Med 2005, 7:571-83; and Strom C M, Mutation detection, interpretation, and applications in the clinical laboratory setting, Mutat Res 2005, 573:160-7, each incorporated by reference. Classification may be based on any suitable combination of sequence-based evidence (e.g., being a truncating mutation), experimental evidence, or genetic evidence (e.g., classified as pathogenic based on genetic evidence if it was a founder variant, or if there was statistical evidence showing the variant was significantly more frequent in affected individuals than in controls; see MacArthur et al., Guidelines for investigating causality of sequence variants in human disease, Nature 2014, 508:469-76). For methods suitable for use in detection of variants detectable by the standard NGS protocol, see Umbarger et al., Next-generation carrier screening, Genet Med 2014, 16:132-40 and Hallam et al., Validation for Clinical Use of, and Initial Clinical Experience with, a Novel Approach to Population-Based Carrier Screening using High-Throughput, Next-Generation DNA Sequencing, J Mol Diagn 2014, 16:180-9, both incorporated by reference.

Functions described above such as sequence read analysis or assembly can be implemented using systems of the invention that include software, hardware, firmware, hard-wiring, or combinations of any of these.

Figure 5:
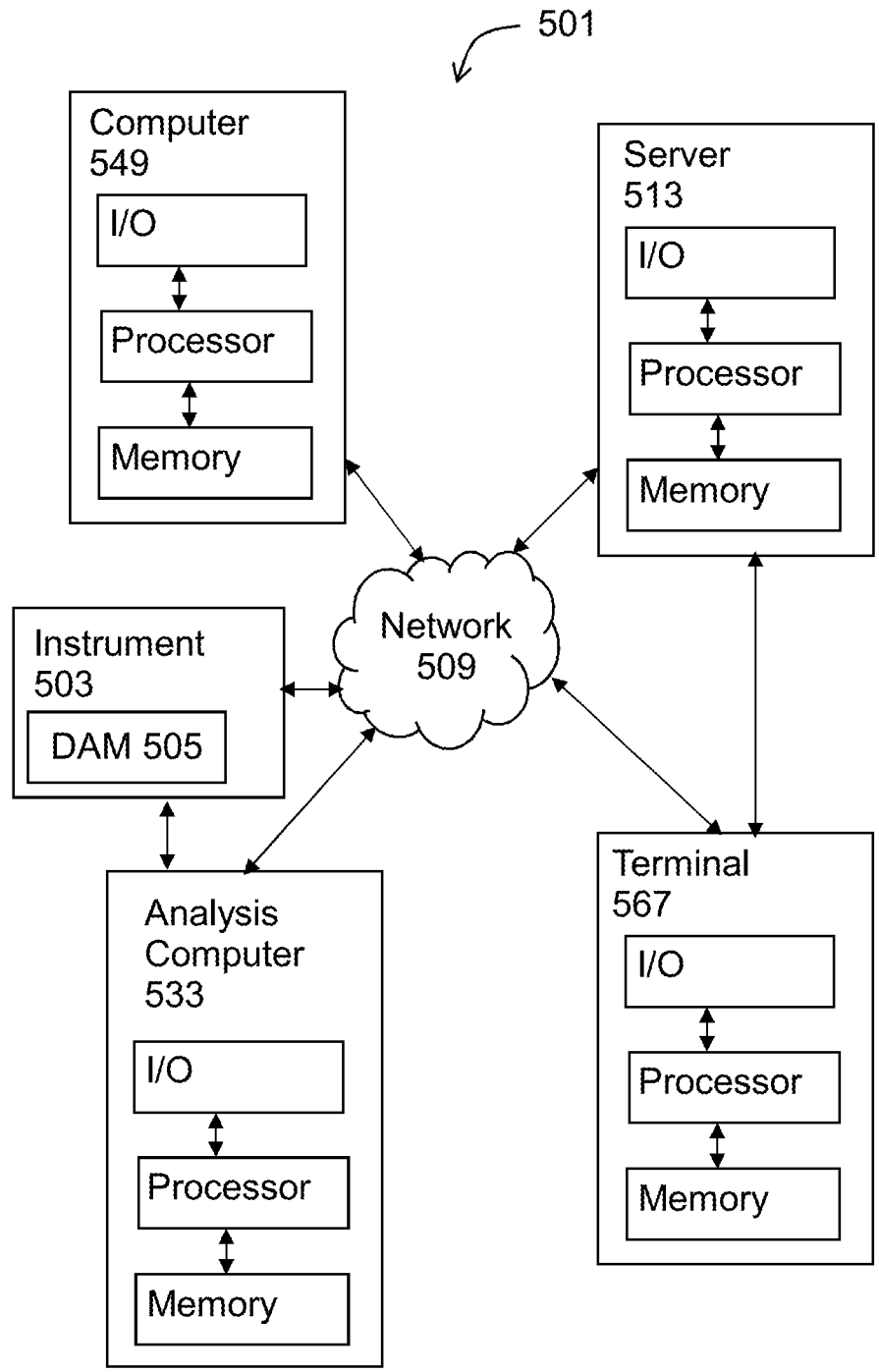
FIG. 5 gives a diagram of a system of the invention.

FIG. 5 gives a diagram of a system 501 according to embodiments of the invention. System 501 may include an analysis instrument 503 which may be, for example, a sequencing instrument (e.g., a HiSeq 2500 or a MiSeq by Illumina). Instrument 503 includes a data acquisition module 505 to obtain results data such as sequence read data. Instrument 503 may optionally include or be operably coupled to its own, e.g., dedicated, analysis computer 533 (including an input/output mechanism, one or more processor, and memory). Additionally or alternatively, instrument 503 may be operably coupled to a server 513 or computer 549 (e.g., laptop, desktop, or tablet) via a network 509.

Computer 549 includes one or more processors and memory as well as an input/output mechanism. Where methods of the invention employ a client/server architecture, steps of methods of the invention may be performed using the server 513, which includes one or more of processors and memory, capable of obtaining data, instructions, etc., or providing results via an interface module or providing results as a file. The server 513 may be engaged over the network 509 by the computer 549 or the terminal 567, or the server 513 may be directly connected to the terminal 567, which can include one or more processors and memory, as well as an input/output mechanism.

In system 501, each computer preferably includes at least one processor coupled to a memory and at least one input/output (I/O) mechanism.

A processor will generally include a chip, such as a single core or multi-core chip, to provide a central processing unit (CPU). A process may be provided by a chip from Intel or AMD.

Memory can include one or more machine-readable devices on which is stored one or more sets of instructions (e.g., software) which, when executed by the processor(s) of any one of the disclosed computers can accomplish some or all of the methodologies or functions described herein. The software may also reside, completely or at least partially, within the main memory and/or within the processor during execution thereof by the computer system. Preferably, each computer includes a non-transitory memory such as a solid state drive, flash drive, disk drive, hard drive, etc. While the machine-readable devices can in an exemplary embodiment be a single medium, the term "machine-readable device" should be taken to include a single medium or multiple media (e.g., a centralized or distributed database, and/or associated caches and servers) that store the one or more sets of instructions and/or data. These terms shall also be taken to include any medium or media that are capable of storing, encoding, or holding a set of instructions for execution by the machine and that cause the machine to perform any one or more of the methodologies of the present invention. These terms shall accordingly be taken to include, but not be limited to one or more solid-state memories (e.g., subscriber identity module (SIM) card, secure digital card (SD card), micro SD card, or solid-state drive (SSD)), optical and magnetic media, and/or any other tangible storage medium or media.

A computer of the invention will generally include one or more I/O device such as, for example, one or more of a video display unit (e.g., a liquid crystal display (LCD) or a cathode ray tube (CRT)), an alphanumeric input device (e.g., a keyboard), a cursor control device (e.g., a mouse), a disk drive unit, a signal generation device (e.g., a speaker), a touchscreen, an accelerometer, a microphone, a cellular radio frequency antenna, and a network interface device, which can be, for example, a network interface card (NIC), Wi-Fi card, or cellular modem.

Any of the software can be physically located at various positions, including being distributed such that portions of the functions are implemented at different physical locations.

System 401 or components of system 401 may be used to perform methods described herein. Instructions for any method step may be stored in memory and a processor may execute those instructions. System 401 or components of system 401 may be used for the analysis of genomic sequences or sequence reads (e.g., detecting deletions and variant calling).

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

What is claimed is:

1. A nucleic acid product comprising:
   a first molecular inversion probe comprising a linked pair of targeting arms designed to hybridize upstream and downstream of a first target in a reference genome;
   a second molecular inversion probe comprising a linked pair of targeting arms designed to hybridize upstream and downstream of a second target in a reference genome, wherein the first and second targets are non-contiguous; and
   an inter-probe region connecting one of the targeting arms of the first molecular inversion probe with one of the targeting arms of the second molecular inversion probe, wherein the second molecular inversion probe and the inter-probe region have been ligated to the first molecular inversion probe to form an inter-probe product;
   wherein at least one of the first and second molecular inversion probes comprises a phosphorothioate base.

2. The nucleic acid product of claim 1, wherein the targeting arms of each molecular inversion probe are configured to hybridize to nucleic acid residues on a same strand of the reference genome.

3. The nucleic acid product of claim 1, wherein the inter-probe region comprises nucleic acid sequence spanning a structural variant on a target nucleic acid.

4. The nucleic acid product of claim 3, wherein the inter-probe region comprises nucleic acid sequence formed by filling in a gap between the two molecular inversion probes along the target nucleic acid using a polymerase.

5. The nucleic acid product of claim 3, wherein the structural variant comprises an insertion, inversion, translocation, or deletion.

6. The nucleic acid product of claim 1, wherein the phosphorothioate base is located in a backbone of the first or second molecular inversion probes.

7. The nucleic acid product of claim 1, wherein the phosphorothioate base is located on the first molecular inversion probe.

8. The nucleic acid product of claim 1, wherein the phosphorothioate base is located on the second molecular inversion probe.

9. The nucleic acid product of claim 1, wherein each of the first and second molecular inversion probes comprises a phosphorothioate base.

10. A probe set comprising a plurality of different molecular inversion probes, each different molecular inversion probe comprising:
   a first targeting arm configured to hybridize upstream of a target in a reference genome;
   a second targeting arm configured to hybridize downstream of a target in a reference genome; and
   a central region flanked by the first and second targeting arms, the central region comprising a phosphorothioate base,
   wherein the target of each different molecular inversion probe is a different location on the reference genome,
   wherein two molecular inversion probes that hybridize by only one targeting arm have been ligated together by their targeting arms into an inter-probe product.

11. The probe set of claim 10, wherein the plurality of molecular inversion probes are configured to tile across the reference genome with each target overlapping with at least one other target on the reference genome.

12. The probe set of claim 10, wherein the first and second targeting arms of each molecular inversion probe hybridize to nucleic acid residues on a same strand of the reference genome.

13. The probe set of claim 10, wherein each molecular inversion probe is configured to covalently close when hybridized to the reference genome by both targeting arms.

14. An inter-probe product nucleic acid molecule comprising:
   a first molecular inversion probe comprising a first 5' targeting arm a first 3' targeting arm; and
   a second molecular inversion probe comprising a second 5' targeting arm and a second 3' targeting arm, wherein the second 3' targeting arm is ligated to the first 5' targeting arm.

15. The nucleic acid molecule of claim 14, wherein the first molecular inversion probe is ligated to the second molecular inversion probe via an extension segment synthesized by a polymerase when the first molecular inversion probe and the second molecular inversion probe were each hybridized to a target by only one probe arm.

16. The nucleic acid molecule of claim 14, wherein the second 3' targeting arm was ligated to the first 5' targeting arm due to the presence of a structural variant.

17. The nucleic acid molecule of claim 16, wherein the structural variant comprises a deletion.

18. The nucleic acid molecule of claim 15, wherein the nucleic acid molecule is present among a plurality of probes including the nucleic acid molecule and a plurality of molecular inversion probes that each have been circularized and include a copy of a portion of the target.

19. The nucleic acid molecule of claim 18, wherein the plurality of probes are useful in a carrier screening assay that can report on variants in a genome of a patient, wherein the reported variants include mutations, short indels between about 1 and tens of base pairs, large deletions.

20. The nucleic acid molecule of claim 18, wherein the plurality of molecular inversion of probes, after being circularized, have been cleaved into linear fragments and attached to barcodes and sequencing adaptors, and further wherein the plurality of probes are attached to the surface of flow cell channels.

* * * * *